United States Patent
Kubota et al.

(10) Patent No.: US 7,378,644 B2
(45) Date of Patent: May 27, 2008

(54) IMAGE READING APPARATUS

(75) Inventors: Mineo Kubota, Kofu (JP); Kazuhito Dobashi, Yamanashi-ken (JP); Koji Ueda, Minami-Alps (JP); Yoshihiro Hanagata, Yamanashi-ken (JP)

(73) Assignee: Nisca Corporation, Yamanashi-Ken (JP)

( * ) Notice: Subject to any disclaimer, the term of this patent is extended or adjusted under 35 U.S.C. 154(b) by 478 days.

(21) Appl. No.: 10/942,909

(22) Filed: Sep. 17, 2004

(65) Prior Publication Data

US 2005/0063871 A1    Mar. 24, 2005

(30) Foreign Application Priority Data

| Sep. 18, 2003 | (JP) | ............................. 2003-326697 |
| Dec. 24, 2003 | (JP) | ............................. 2003-428193 |
| Dec. 24, 2003 | (JP) | ............................. 2003-428194 |
| Dec. 24, 2003 | (JP) | ............................. 2003-428195 |
| Dec. 24, 2003 | (JP) | ............................. 2003-428196 |
| Aug. 3, 2004 | (JP) | ............................. 2004-226355 |
| Aug. 3, 2004 | (JP) | ............................. 2004-226356 |

(51) Int. Cl.
H04N 1/04    (2006.01)

(52) U.S. Cl. .................. 250/234; 250/208.1; 358/474; 358/497

(58) Field of Classification Search ............. 250/208.1, 250/234, 235; 358/474, 487, 494, 497, 505, 358/506

See application file for complete search history.

(56) References Cited

U.S. PATENT DOCUMENTS 5,814,809 A * 9/1998 Han ........................ 250/208.1

OTHER PUBLICATIONS

Patent Abstracts of Japan; Publication No. 07-140561; Publication Date: Jun. 2, 1995; Applicant: Fuji Photo Film Co., Ltd.; Title: Image Forming Device.
Patent Abstracts of Japan; Publication No. 09-179214; Publication Date: Jul. 11, 1997; Applicant: Fuji Photo Film Co., Ltd.; Title: Image Forming Device.
Patent Abstracts of Japan; Publication No. 06-189063; Publication Date: Jul. 8, 1994; Applicant: Ricoh Klemex Corp.; Title: Book Original Reader.
Patent Abstracts of Japan; Publication No. 07-303173 (Patent umber 3410810); Publication Date: Nov. 14, 1995; Applicant: Ricoh Co., Ltd.; Title: Original Reader.
Patent Abstracts of Japan; Publication No. 09-121837; Publication Date: May 13, 1997; Applicant: Densei KK; Title: Apparatus for Measuring Number of Colonies.

* cited by examiner

*Primary Examiner*—Kevin Pyo
(74) *Attorney, Agent, or Firm*—Manabu Kanesaka

(57) ABSTRACT

An image reading apparatus includes a stage for placing a specimen. The stage moves in first directions between a setting position where the specimen is placed and removed and a reading position for reading the specimen. The image reading apparatus also includes a light source for irradiating light onto the specimen on the stage, a photoelectric conversion device having a line shape for photo-electrically converting the light reflected from the specimen, an optical device for guiding the light from the specimen to the photoelectric conversion device, a carriage mounting the optical device, and an apparatus frame for movably supporting the stage and the carriage. The carriage moves along the stage in second directions substantially same as the first direction.

4 Claims, 28 Drawing Sheets

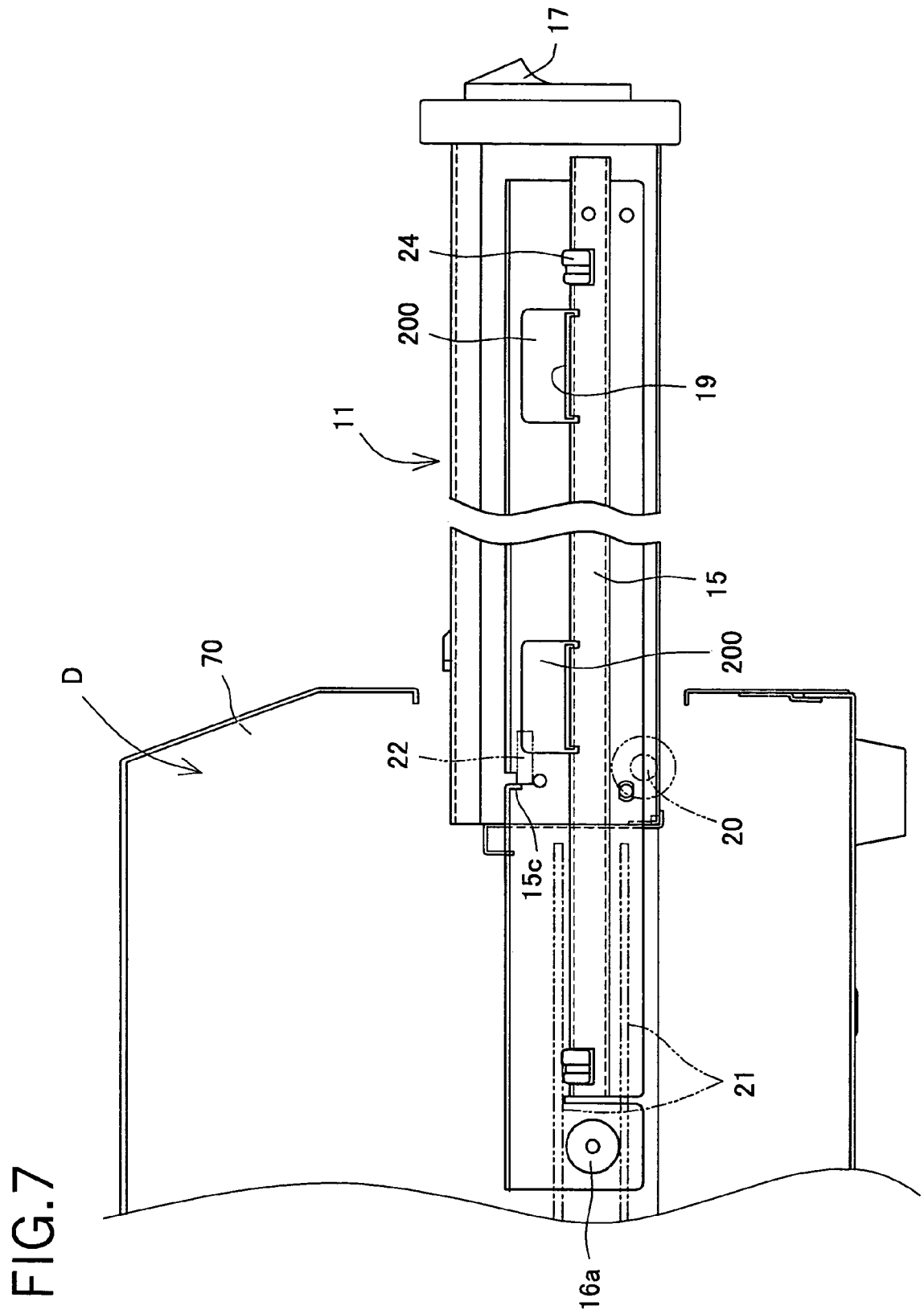

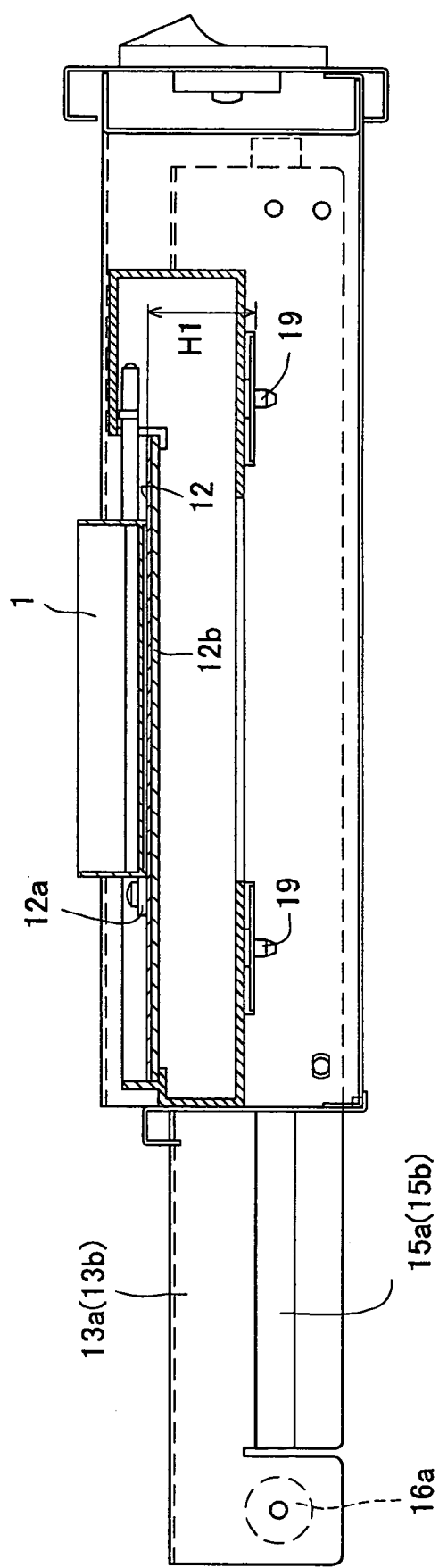

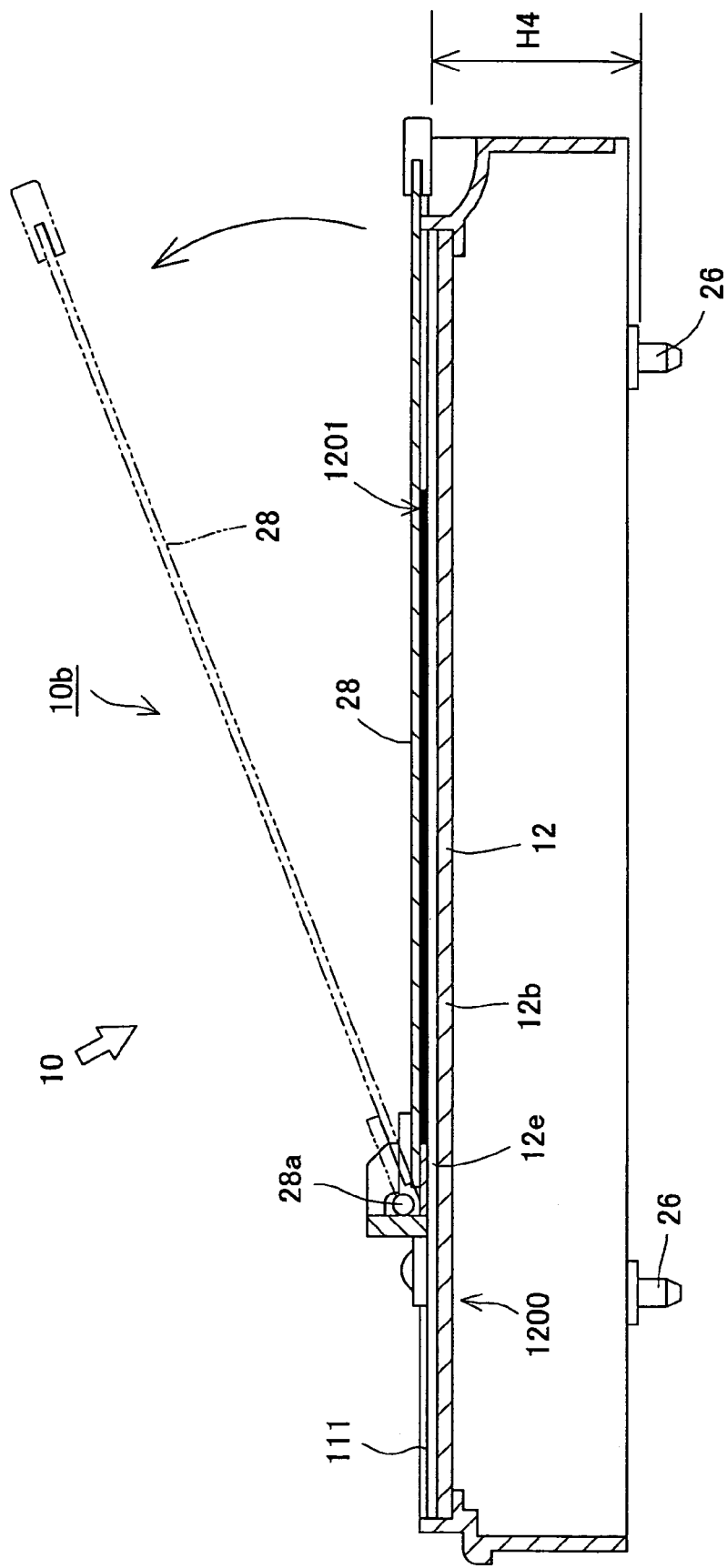

FIG. 16
(a) Initial Processing when Power is Turned On
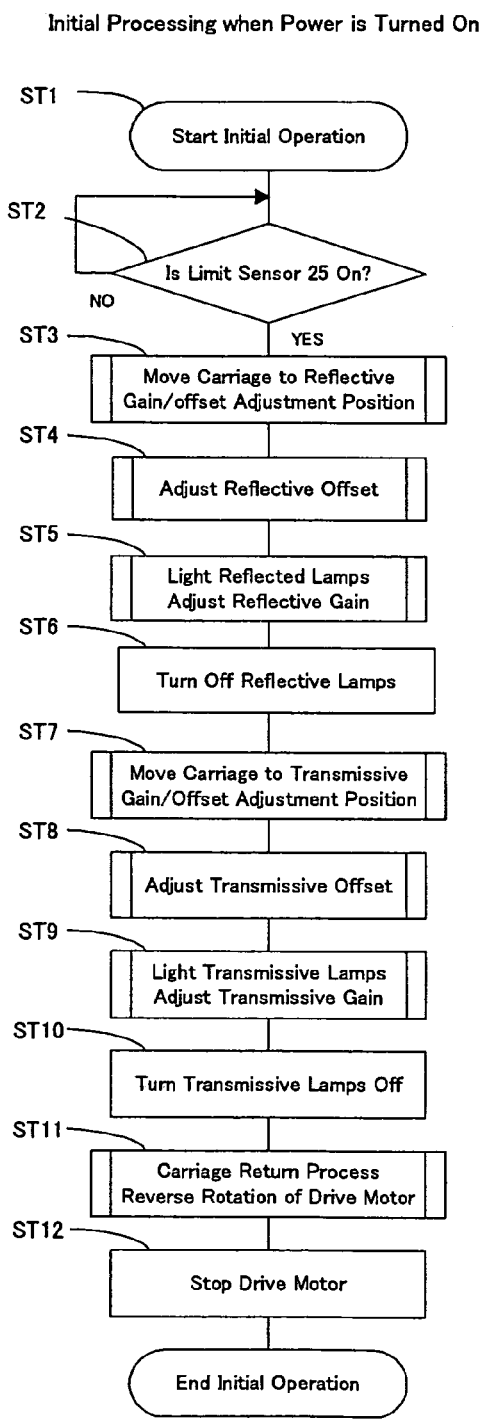
(b) Reading Operation
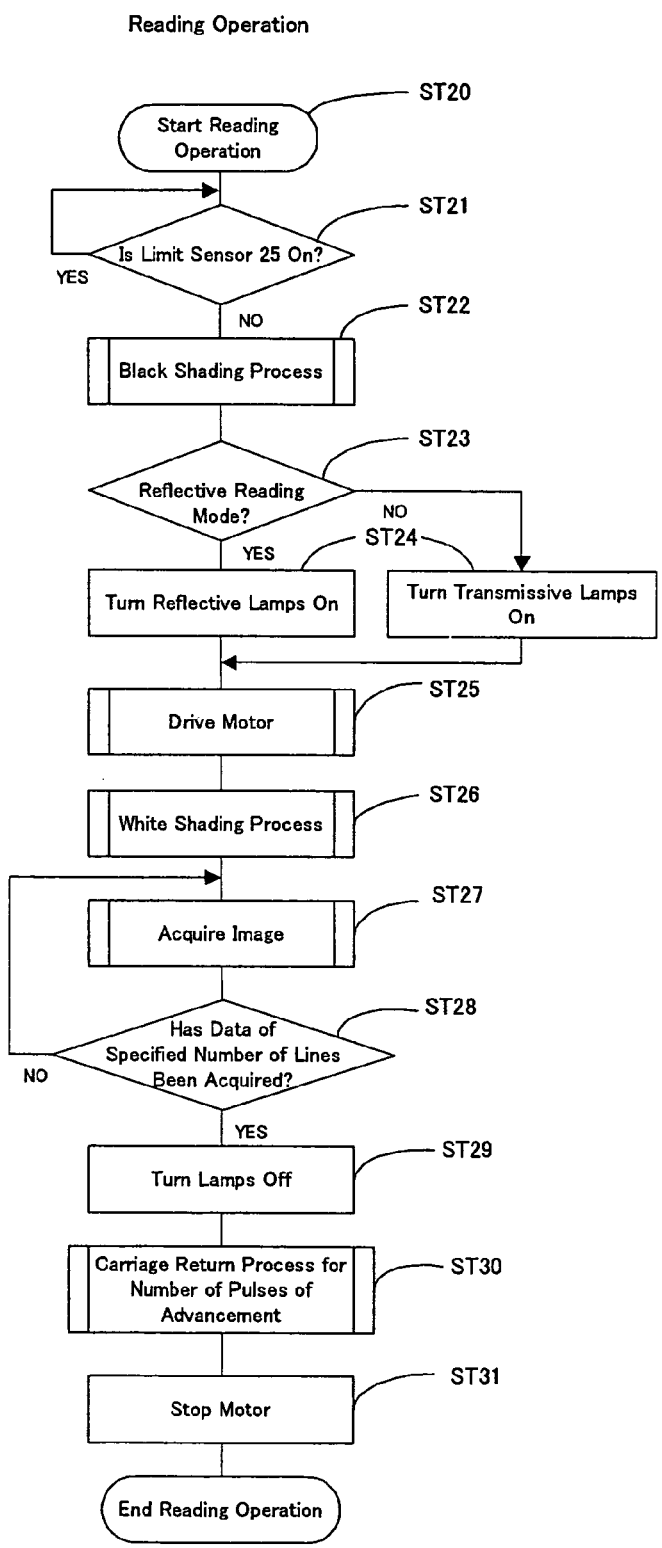

IMAGE READING APPARATUS

BACKGROUND OF THE INVENTION AND RELATED ART STATEMENT

The invention relates to an image reading apparatus for optically forming a flat image such as a sheet or a three-dimensional image such as a liquid surface on a photoelectric conversion element, so that the photoelectric conversion element electrically reads such an image. More particularly, the present invention relates to an image reading apparatus for reading media such as bacteria or microorganisms for analysis.

Generally, an optical microscope has been used for observing a material cultivated on a medium such as liquid and a sheet to analyze a propagation state of bacteria or microorganisms. In recent years, a new inspection system has been available in which a photoelectric sensor such as CCD electrically reads such a medium and an image processing apparatus such as a computer analyzes data, and then the data is stored.

Conventionally, Japanese Patent Publication (Kokai) No. 09-121837 has disclosed a colony count measuring apparatus for reading a three-dimensional object. In the colony count measuring apparatus, a CCD camera is mounted on a stage such as a Petri dish for placing a specimen to be viewed. That is, a flat sensor is used for capturing an image. In this case, it is necessary to provide an enough distance between the specimen and the camera (between the stage and the camera) to obtain an entire image of the specimen. Also, it is necessary to use a light source with a high output for illuminating the entire specimen, thereby increasing a size of the apparatus.

Japanese Patent Publications (Kokai) No. 07-140561 and No. 09-179214 have disclosed other apparatus for reading a three-dimensional object. In the image forming apparatus, an optical system formed of a bar-shaped light source, a lens and a mirror is arranged above a stage for placing a specimen, and the optical system moves to sequentially read an image of the specimen in line. With this type of sequential reading method, it is possible to bend a light path with the mirror, and it is not necessary to use a light source with a high output, thereby making the apparatus smaller than the apparatus using the CCD camera disclosed in Japanese Patent Publication (Kokai) No. 09-121837.

In the image forming apparatus disclosed in Japanese Patent Publications (Kokai) No. 07-140561 and No. 09-179214, it is necessary to provide a space between the stage and the optical system for placing and adjusting the specimen at a predetermined reading position on the stage, thereby increasing a size of the apparatus. The apparatus is provided with a mechanism for mounting the optical system to be movable freely up and down so that a focus position can be freely changed. The mechanism moves the optical system (scanning unit) itself up and down, or moves a frame supporting the optical system up and down, so that the mechanism tends to be large, thereby increasing a size of the apparatus.

Japanese Patent Publication (Kokai) No. 06-189063 has disclosed a reading apparatus having a stage for placing an original to be viewed formed of a drawer mechanism moving between a reading position inside the apparatus and a setting position for placing the original on the stage outside the apparatus. In the reading apparatus, it is possible to adjust the object (original) to be viewed at the setting position outside the apparatus. Accordingly, it is possible to make the apparatus compact as compared with the image forming apparatus disclosed in Japanese Patent Publication (Kokai) No. 07-140561, in which it is necessary to provide a large space between the stage and the optical system at the reading position for the adjustment.

In the reading apparatus disclosed in Japanese Patent Publication (Kokai) No. 06-189063, the original is pressed against the reading unit so that an image surface of the original (specimen) is located at a focus position of the reading unit. Accordingly, it is difficult to handle a specimen in a liquid state or a gel state. Also, the reading apparatus is provided with a mechanism for rotating the stage to press the original against the reading unit, thereby increasing a size of the apparatus.

Japanese Patent No. 3410810 has disclosed a reading apparatus having a drawer mechanism for moving a stage between a reading position and a setting position, similar to the reading apparatus disclosed Japanese Patent Publication (Kokai) No. 06-189063. In the reading apparatus, the original is pressed against a reading unit so that an image surface of an original (specimen) is located at a focus position of the reading unit. Accordingly, it is difficult to handle a specimen in a liquid state or a gel state. The reading apparatus is also provided with a mechanism for moving the original up and down, thereby increasing a size and cost of the apparatus.

In view of the problems described above, an object of the present invention is to provide a compact image reading apparatus for reading a three-dimensional object such as liquid.

Another object of the present invention is to provide a compact and low-cost apparatus having a simple mechanism for adjusting a focus position.

Further objects and advantages of the invention will be apparent from the following description of the invention.

SUMMARY OF THE INVENTION

In order to attain the objects described above, in an image reading apparatus according to a first aspect of the present invention, a stage and a carriage move in a same direction, or the stage, the carriage and a light source move in a substantially same direction. Accordingly, a space for a moving mechanism of the stage can be used for a moving region of the carriage or the light source, thereby making the apparatus compact.

In the image reading apparatus, a drive motor may be arranged below the moving region of the carriage and at least a portion thereof is overlapped with a scanning region of the carriage in a vertical direction. Alternatively, the drive motor may be arranged below the moving region of the carriage and above the moving region of the light source unit, and at least a portion thereof is overlapped with the moving region of the carriage or the moving region of the light source unit in the vertical direction. With this structure, it is possible to use a space below or above the moving regions of the carriage and the light source for arranging the drive motor, thereby decreasing a size of the apparatus.

The image reading apparatus may be provided with speed selection means for selecting a moving speed of the stage, so that the stage moves at various speeds corresponding to the speed selected by the speed selection means. Accordingly, it is possible to select the moving speed of the stage according to a state (such as liquid or sheet) of the specimen (sample) to be viewed, thereby improving operability.

According to a second aspect of the present invention, an image reading apparatus is provided a plurality of stages arranged such that each of the stages has a stage surface at a different height. An apparatus frame is structured such that at least one of the stages can be selectively mounted. Accordingly, it is possible to adjust a focus position with a simple configuration, thereby reducing a size and cost of the image reading apparatus. With this simple configuration, even if the stages are arranged to be movable between a setting position and a reading position, it is possible to reduce a size and weight of the stage support means for supporting the stages.

In the image reading apparatus, the stages and a carriage move in a same direction. Accordingly, it is possible to overlap a moving region of the carriage with an extended portion of the holder member for supporting the stages, thereby making the apparatus compact. Further, a drive motor may be arranged to overlap with a moving region of the scanning carriage, thereby further configuring the image reading apparatus to be compact.

Further, the stages for placing objects to be read are detachably mounted to a mounting member provided on the apparatus frame, and a plurality of the stages having the stage surfaces at different mounting heights is selectively attached to the mounting member according to a shape and state of the objects. Therefore, it is possible to easily set even a liquid object at a predetermined reading position. Also, it is possible to accurately set the object for focusing without a special focusing mechanism, thereby reducing a size and cost of the image reading apparatus.

BRIEF DESCRIPTION OF THE DRAWINGS

FIGS. 6A and 6B are views showing a holder member for supporting the stage of the image reading apparatus shown in FIG. 1, wherein FIG. 6A is a plan view thereof, and FIG. 6B is a side view thereof;

FIG. 7 is a view showing the holder member at a setting position in the image reading apparatus shown in FIG. 1;

FIGS. 8A and 8B are views showing a configuration of the stage, wherein FIG. 8A is a longitudinal sectional view thereof, and FIG. 8B is a plan view thereof;

FIG. 9 is a view showing the stage shown in FIGS. 8A and 8B mounted to the holder member;

FIGS. 10A and 10B are views showing a stage height adjustment member, wherein FIG. 10A is a plan view thereof, and FIG. 10B is a longitudinal sectional view thereof;

FIG. 11 is a longitudinal sectional view of a configuration of a stage different from that shown in FIGS. 8A and 8B;

FIG. 16A is a flowchart for explaining an initialization process in an operation of the image reading apparatus shown in FIG. 1, and FIG. 16B is a flowchart for explaining an image reading process in the operation of the image reading apparatus shown in FIG. 1;

DETAILED DESCRIPTION OF PREFERRED EMBODIMENTS

Figure 1:
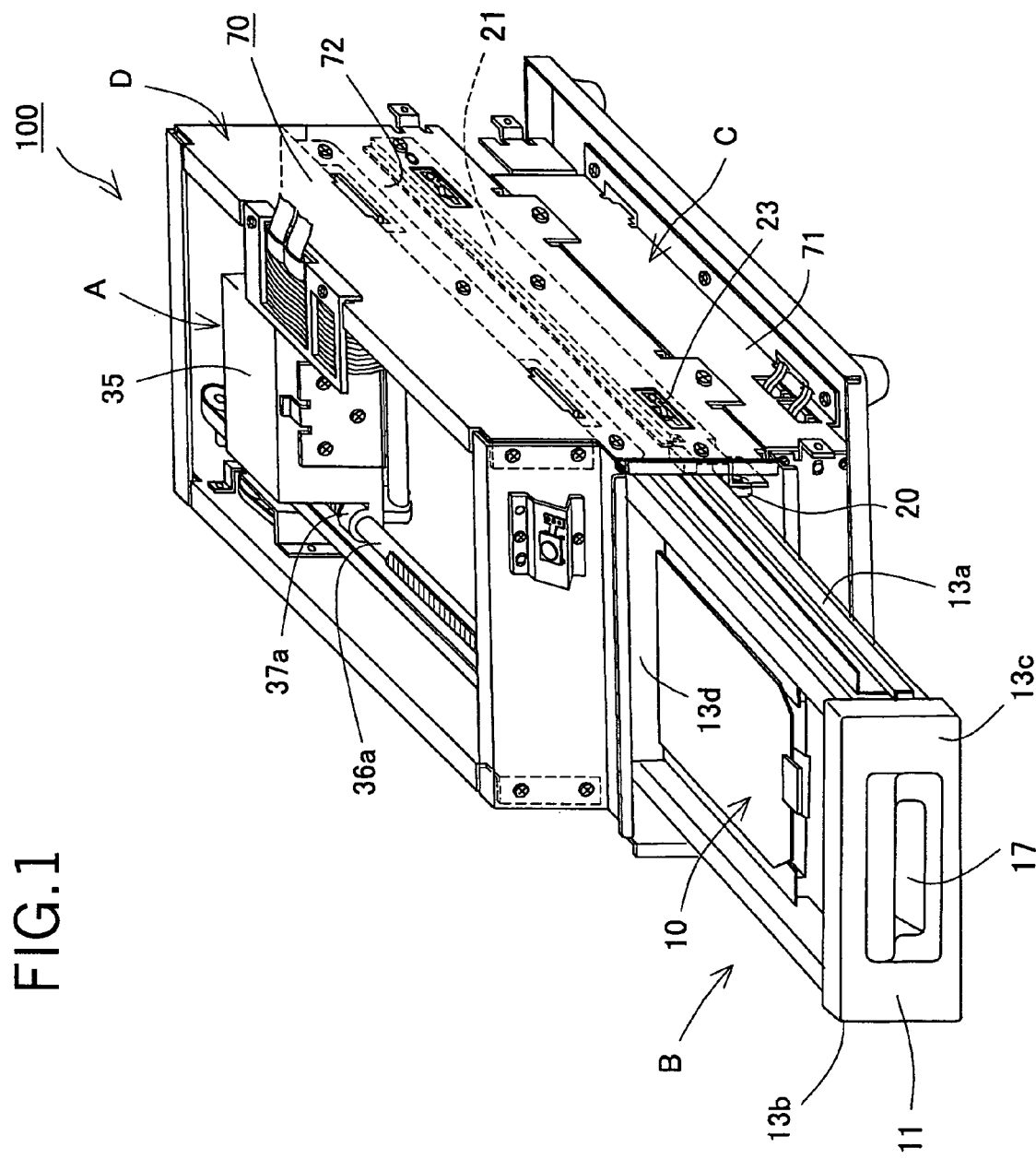
FIG. 1 is a perspective view showing an overall configuration of an image reading apparatus according to a first embodiment of the present invention.
Figure 2:
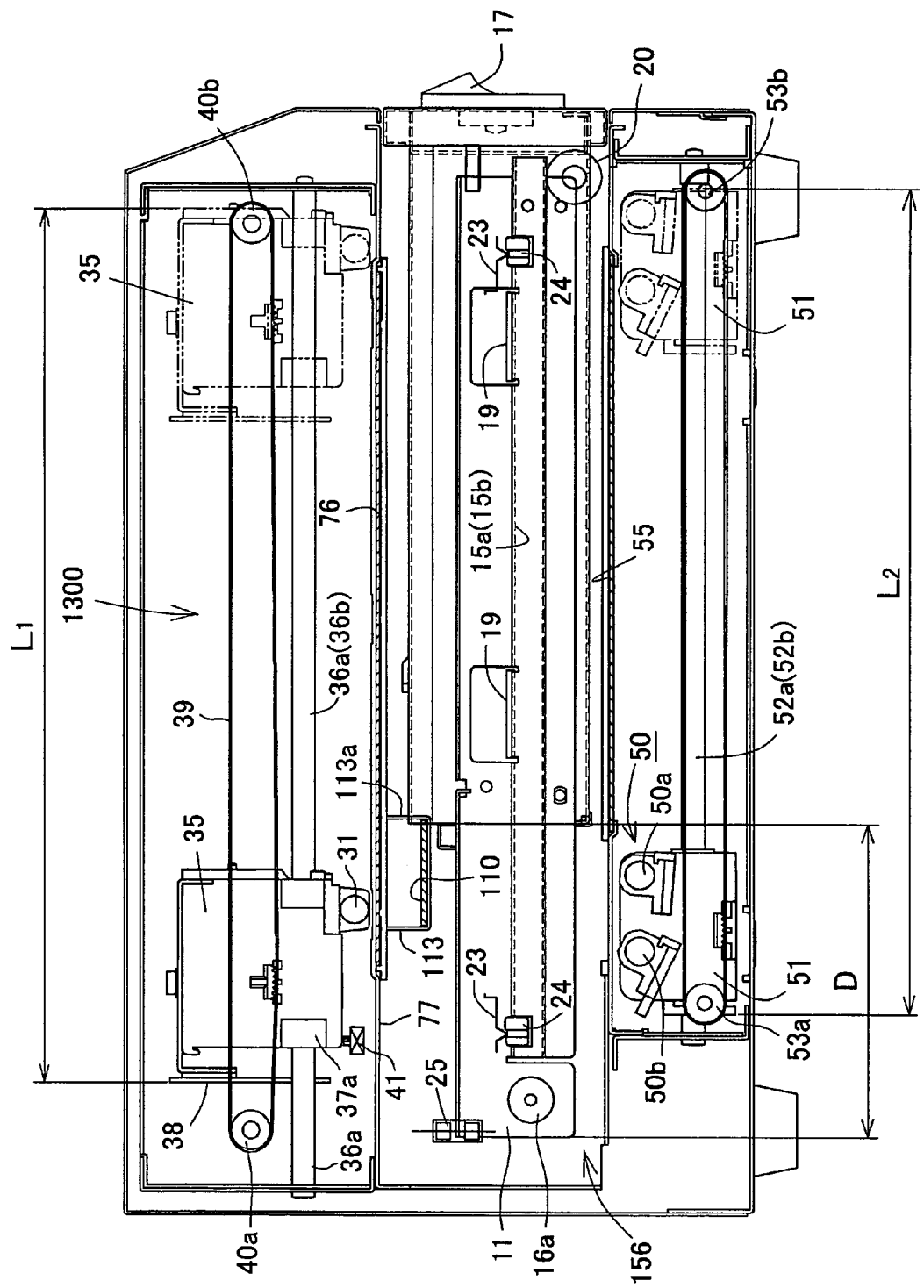
FIG. 2 is a longitudinal sectional view of a central portion of the image reading apparatus shown in FIG. 1.
Figure 3:
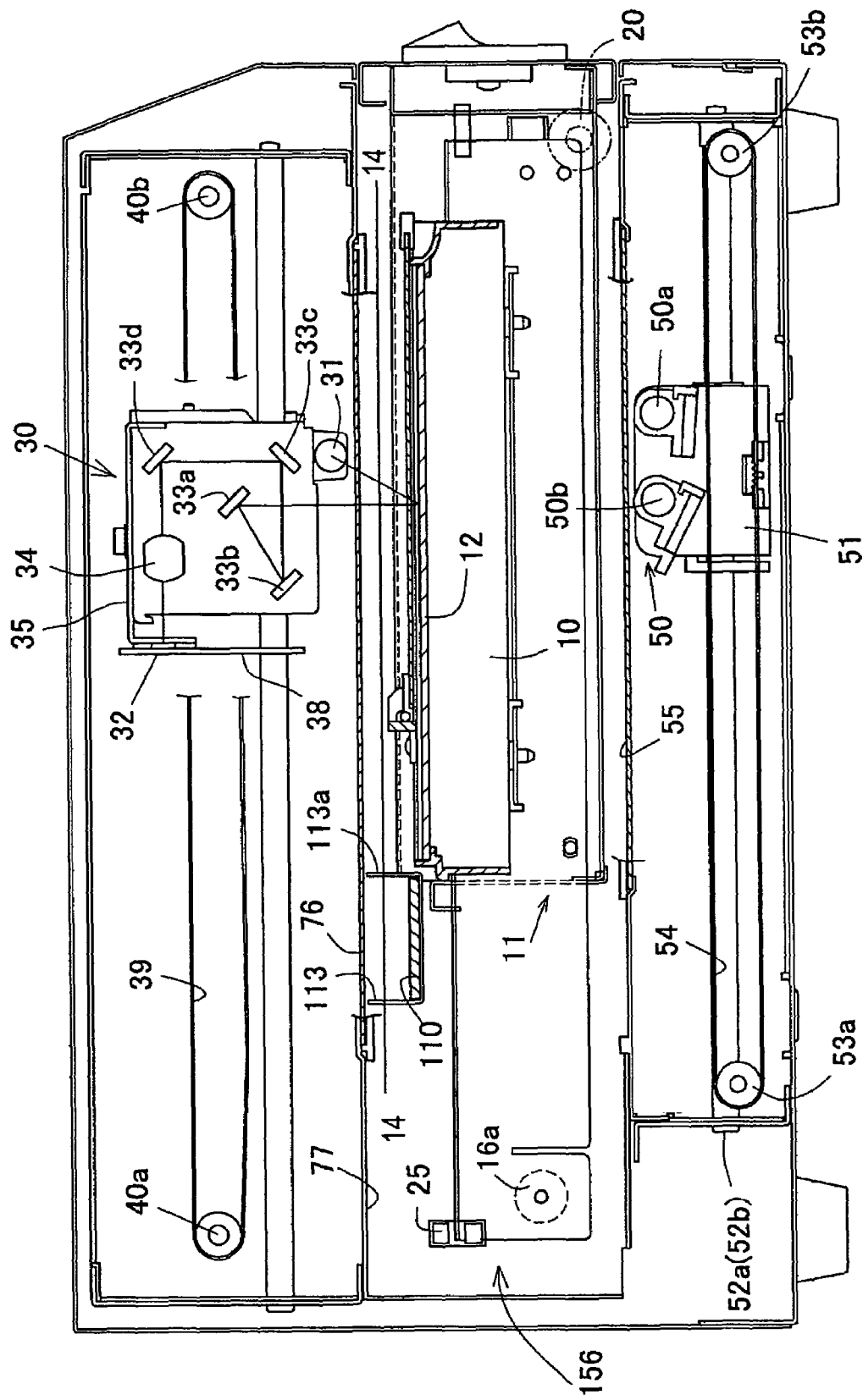
FIG. 3 is a view showing an essential portion of a scanning unit and a transmissive light source unit shown in FIG. 2.

Hereunder, preferred embodiments of the invention will be explained with reference to the accompanied drawings. FIG. 1 shows an overall configuration of an image reading apparatus 100 according to an embodiment of the present invention. FIG. 2 is a longitudinal sectional view of a central portion of the apparatus, and FIG. 3 shows a detail of the central portion. The image reading apparatus 100 shown in FIG. 1 comprises a scanning unit A disposed in a housing D for optically reading a specimen; a stage unit B for placing the specimen; and a transmissive light source unit C for irradiating light onto the specimen. The housing D is formed of a box-shaped apparatus frame 70. The transmissive light source unit C; the stage unit B; and a scanning unit are arranged vertically in this order from a bottom of the apparatus frame 70. A configuration of each of these units is described below.

A photo-optical system reads an image of the specimen using photoelectric conversion means. The photo-optical system is formed of a line sensor 32 (photo-electric conversion means) for photo-electrically converting light reflected from the specimen; and an optical system 30 (optical means) such as a mirror and a lens for guiding light from the specimen to the line sensor 32. The lens collects light reflected from the specimen and the line sensor 32 electrically convert light to obtain image data. The light source shown in FIG. 2 and FIG. 3 is provided with a reflective light source 31 (first light source) for irradiating light from a front side of the specimen (upper side of the stage), and a transmissive light source 50 (second light source) for irradiating light from a backside of the specimen (lower side of the stage).

When the specimen is a sheet or a translucent (opaque) material such as a culture medium disposed on a sheet, the reflective light source 31 is used to irradiate the specimen, and the optical system 30 guides reflected light to the line sensor 32. When the specimen is transparent (light passing therethrough) such as bacteria cultivated in a transparent container such as a Petri dish or a transparent film sheet, the transmissive light source 50 is used to irradiate the specimen, and the optical system 30 guides light passing therethrough to the line sensor 32.

When the apparatus specification is limited to opaque specimens, the apparatus is provided with only the first light source (reflective light source) 31. When the apparatus specification is limited to transparent specimens, the apparatus is provided with only the second light source (transmissive) 50. Since the photoelectric conversion means is a line sensor, the light source is formed in a bar shape and includes a halogen lamp, fluorescence light, and LED array. In the embodiment, a Xenon lamp is used because of low-cost and easy replacement.

As shown in FIG. 3, the optical system 30 is formed of the image forming lens 34 and the reflective mirrors 33a to 33d for guiding light to the image forming lens 34 to form a conventionally known light path. In the embodiment, the four mirrors 33a, 33b, 33c, and 33d are provided for guiding light from the specimen to the image forming lens 34, thereby making the light path short (See FIG. 3). The optical system 30 may have other configurations using lenses and mirrors to form an image of the specimen on the line sensor 32 arranged at a predetermined position. For example, a lens array formed of a bar-shape lens such as a Selfoc lens arranged in line may be provided for guiding light from the specimen directly to the line sensor 32.

The line sensor 32 is formed of a plurality of photoelectric conversion elements such as CCDs (charged coupled device) arranged in line for sequentially scanning the specimen in line. The line sensor 32 is provided with a predetermined number of photoelectric conversion elements corresponding to a reading resolution. The line sensor 32 receives light from the specimen and generates an electrical potential to be sequentially transferred per pixel, so that an image of the specimen is obtained as electrical data. Accordingly, an array direction of the photoelectric conversion elements of the line sensor 32 becomes a main scanning direction.

Figure 4:
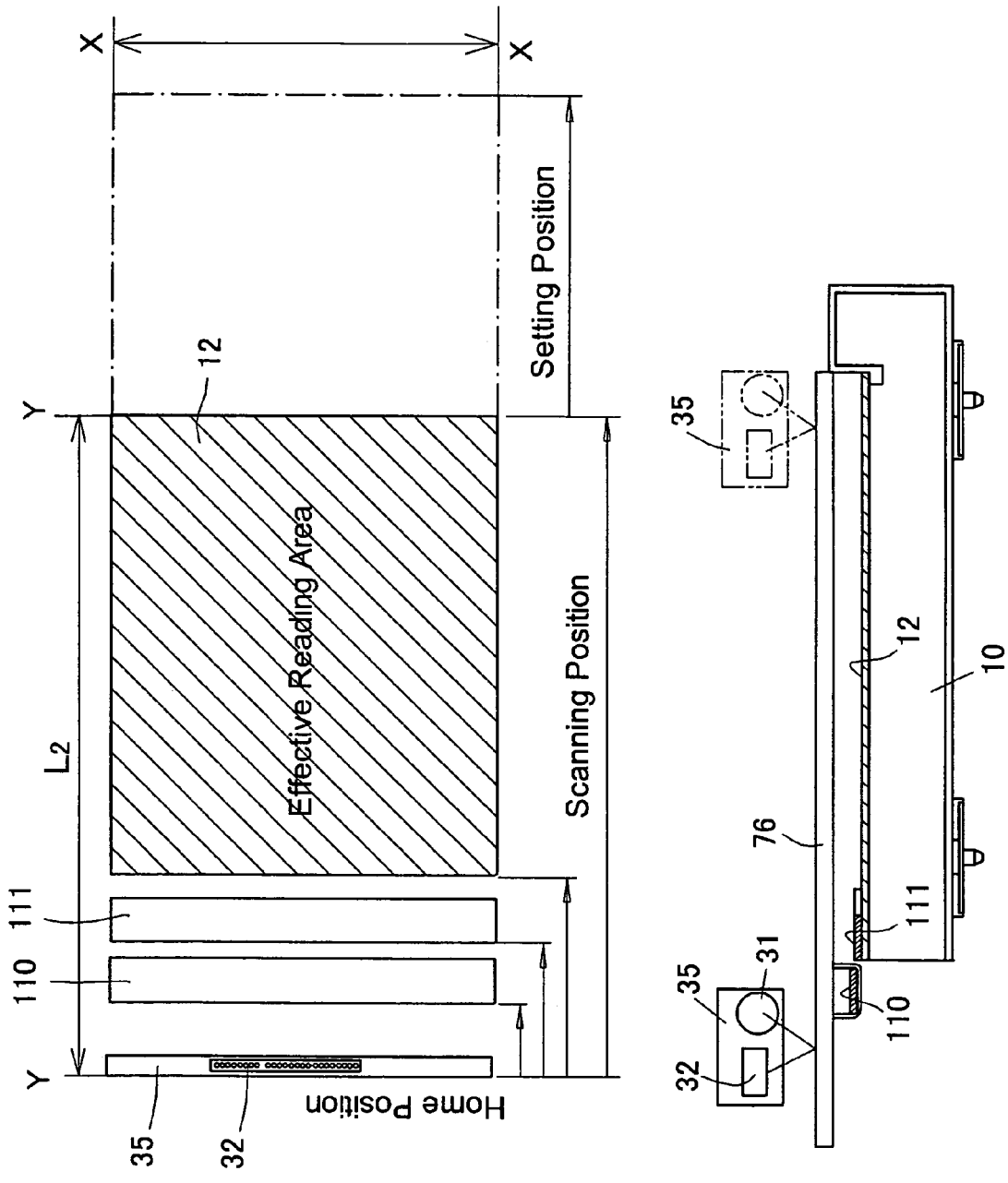
FIG. 4 is a view showing a structure of a stage in the image reading apparatus shown in FIG. 1.

As shown in FIG. 4, the line sensor 32 is arranged in X-X directions, and a carriage (described below) moves in Y-Y directions. In the embodiment, a sub-scanning direction, i.e. the Y-Y directions, is set to be longer than the main scanning direction, i.e. the X-X directions. A movement length L2 of the carriage (described below) is set to be longer than a main scanning direction length L1 of the carriage (L1<L2). Therefore, the carriage 35 sequentially reads the specimen in line while moving from a home position indicated by solid line to a position indicated by hidden line in the arrow direction shown in the drawing. As a result, an effective reading area (shaded area shown in FIG. 4) becomes rectangular.

A configuration of the scanning unit A having the line sensor 32 for scanning the specimen will be described next. The scanning unit A is provided with a carriage 35 formed of a molded plastic in an appropriate shape with little change over time under various environments. The carriage 35 is provided with at least a portion of the elements constituting the optical system 30. The system is arranged such that when the carriage 35 moves, light led to the line sensor 32 scans the specimen. As shown in FIG. 3, in the embodiment, the carriage 35 is provided with the reflective light source 31, the optical system 30 (mirrors 33a, 33b, 33c, and 33d, and image forming lens 34), the line sensor 32, and a substrate 38 mounted with the line sensor 32.

As a different scanning method, two carriages, i.e. a first and second carriage, may be provided. In this case, a mirror is mounted on one of the two carriages for reflecting light from a light source and the specimen, and two mirrors are mounted on the other of the two carriages for deflecting light from the mirror. The second carriage moves at a speed half of that of the first carriage to scan a flat image. A variety of optical systems can be mounted on the carriage 35, and either one can be employed. When the apparatus specification is limited to transparent specimens, it is not necessary to provide the reflective light source 31.

The carriage 35 is movably mounted to the apparatus frame 70. The carriage 35 shown in FIG. 1 to FIG. 3 is slidably supported on a carriage guide member 36 (first guide member) provided on the apparatus frame 70. The first guide member 36 is composed of a pair of rod members 36a and 36b extending parallel to each other. The rod member 36a shown in FIG. 1 and the rod member 36b (not shown) parallel thereto are fastened to opposite side plates of the apparatus frame 70. A bearing 37a integrated with the carriage 35 (see FIG. 2) engages the rod member 36a, and the rod member 36b is fitted in a bearing of the carriage 35 on the opposite side.

In this way, the carriage 35 is movably supported along the rod members 36a and 36b to move in the left and right directions in FIG. 2. Note that the first guide member 36 may be formed of one rod member for supporting the carrier 35 and a rail surface of a guide rail arranged parallel to the rod member for supporting a portion of the carriage 35 (for example, a portion of the flooring). The substrate 38 is mounted to the carriage 35, and is provided with the line sensor 32, a heat radiation plate (not shown), and a harness wire for transmitting an output signal of the line sensor 32.

The carriage 35 is connected (fastened) to a drive belt 39 placed between a pair of pulleys 40a and 40b attached to the apparatus frame 70. One of the pulleys is connected to a drive motor 90 (described below) capable of both forward and reverse rotations. When the drive motor 90 rotates in the forward and reverse directions, the carriage 35 moves back and forth along the first guide member 36 in the left and right directions in FIG. 2. A position sensor 41 (see FIG. 2) is disposed on a moving path of the carriage 35, and sends a detection signal to control the drive motor 90. In the embodiment, the sensor 41 is mounted to the apparatus frame 70, so that the sensor 41 detects a portion of the carriage at the home position indicated by solid line in FIG. 2.

The stage unit B having the following configuration is arranged below the carriage 35 (scanning unit A). The stage unit B is formed of the stage 10 (stage member) for setting the specimen and a holder member 11 (stage holding means) for supporting the stage 10. As shown in FIG. 2, the holder member 11 is supported on the apparatus frame 70. At least two stages 10 are provided, and each thereof has a stage surface 12 for setting the specimen. One of the stages, i.e. a stage 10a (see FIGS. 8A and 8B), has a structure for setting a liquid specimen in a container such as a Petri dish, and the other stage, i.e. a stage 10b (see FIG. 11), has a structure for setting a sheet specimen. Each of the stages 10a and 10b has a height in a vertical direction such that the specimen is placed at a predetermined position in the height direction corresponding to a predetermined focus position. A configuration of each of the stages 10 will be described below.

Figure 6A:
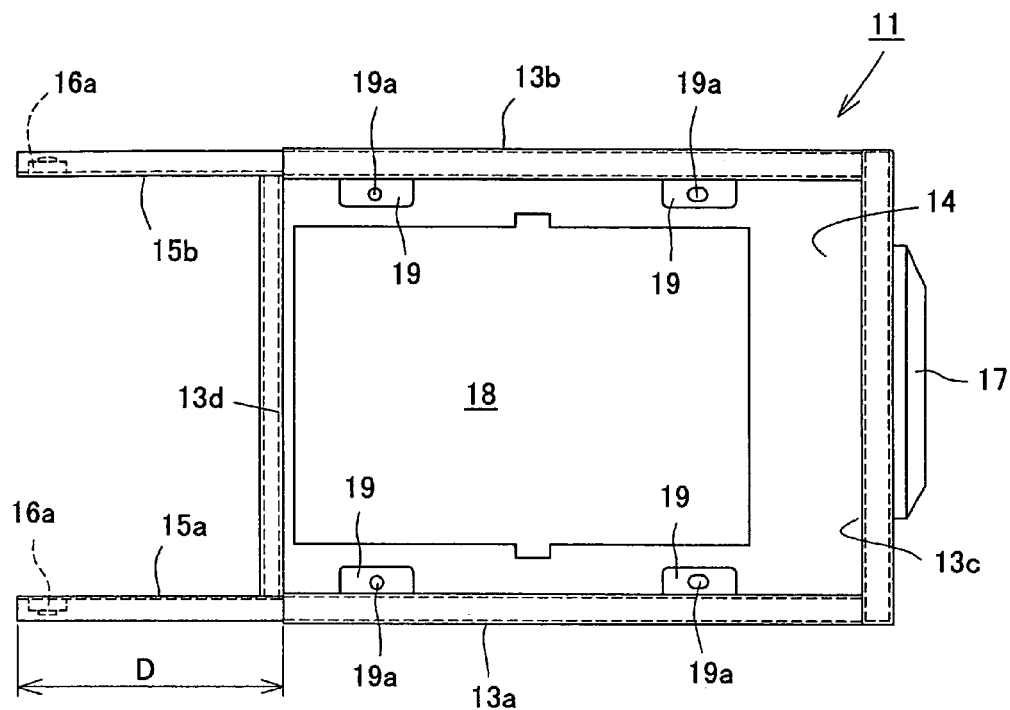
Figure 6B:
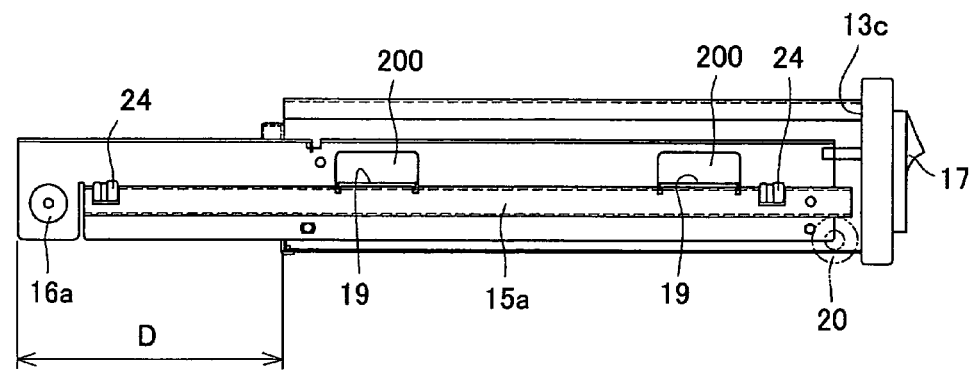

As shown in FIGS. 6A and 6B, the holder member 11 is formed in a substantially box shape having plate-shape members arranged in a frame shape, and is slidably supported on the apparatus frame 70. That is, the holder member 11 comprises a pair of side plates 13a and 13b facing each other and extending in parallel to the moving direction (sub-scanning direction) of the carriage 35 and a pair of side plates 13c and 13d connected to the side plates 13a and 13b to form a square box shape. Also, the holder member 11 has a bottom plate 14 firmly connected to each of the side plates 13 with spot welding. The side plates 13a and 13b are provided with channel shaped rail members 15a and 15b (substantially U-shape cross-section). The rail members 15a and 15b are accurately mounted to the side plates 13a and 13b, so that left and right sides of the moving direction of the carriage 35 are accurately maintained in parallel. As shown in FIG. 6A, the rail members 15a and 15b are formed to extend toward back by a length D from a region where the stages are supported.

Portions of the rail members 15a and 15b are bent, and the bent portions are inserted into the holder member 11 through slits 200 formed in the side plates 13a and 13b, so that the bent portions form mounting surfaces 19. The mounting surfaces 19 are formed on at least one location on each of the rail members 15a and 15b. As shown in FIG. 6A, in the embodiment, the mounting surfaces 19 are formed at four locations at the same height in the height direction.

The stages 10 (described below) are mounted to the mounting surfaces 19. The mounting surfaces 19 are integrated with the rail members 15, thereby reducing the number of components to minimize overlap tolerance (sum of tolerance of each part) and a shift of the specimen relative to the focus position. Also, the side plates 13a and 13b are provided with sliding rollers 16a sliding on guide members (described below) of the apparatus frame 70. An opening 18 is formed in the bottom plate 14, so that the transmissive light source irradiates light onto the specimen. A handle 17 is mounted to the side plate 13c.

As shown in FIGS. 1, 2, and 7, guide rollers 20 contacting the rail members 15a and 15b to rotate thereon are mounted on the apparatus frame 70 at positions indicated by hidden lines in FIG. 6B. A pair of guide members 21a and 21b (second guide member 21) having a substantially U-shape cross-section is attached to the apparatus frame 70 for contacting and guiding the rollers 16a and 16b disposed on the rail numbers 15. Accordingly, the holder member 11 moves along the second guide members 21 provided on the apparatus frame 70 in the left to right direction, so that the stages 10 move between the reading position shown in FIG. 2 and the setting position shown in FIG. 7 using the handle 17.

The second guide member 21 is arranged in parallel to the first guide member 36 along the same direction. The stages 10 are located at the same position in the height direction at the setting position and the reading position. That is, the stages 10 move on the same plane in the moving region between the setting position and the reading position. Also, the carrier 35 is always located at the same position in the height direction in the moving region from the home position to the reading position. That is, the carriage 35 moves on the same plane. Accordingly, the stages 10 move on the plane parallel to the plane on which the carriage 35 moves with a distance in between in the vertical direction.

As described above, the rail members 15 of the holder member 11 extend from the region supporting the stages 10 by the length D. As shown in FIG. 7, the rail members 15 are fitted in the guide members 21 of the apparatus frame 70 for holding the holder member 11 not to fall out when the holder member 11 is drawn out from the setting position. Accordingly, as shown in FIG. 2, the apparatus becomes longer due to the extended portion (length D) of the rail member 15. In the embodiment, the carriage 35 moves in the direction parallel to (same as) the direction that the holder member 11 moves, so that the moving region L1 of the carriage 35 overlaps with the extended portion D of the holder member 11 in the vertical direction, thereby reducing a size of the apparatus. The extended portion D of the holder member 11 also overlaps with the moving region L2 of the second carriage 51 in the vertical direction.

The holder member 11 is controlled in the following way to be located between the predetermined reading position (positions, i.e. reading positions shown in FIG. 2, and FIG. 3) where the carriage 35 scans and reads the specimen placed on the stage 10 and the setting position (position shown in FIG. 7) where the specimen is placed on and removed from the stage 10. As shown in FIG. 7, at least one stopper portion 15c formed of a bent piece is provided on the rail member 15, and a stopper 22 (formed of a hard plastic) is provided on the second guide members 21 at a side of the apparatus frame 70 for abutting against the bent piece. Accordingly, the stopper 22 prevents the holder member 11 from falling outside of the housing D when the holder member 11 is at the setting position.

The image reading apparatus 100 is provided with holding means for holding the holder member 11 at the reading position. The holding means is composed of springs 23 such as leaf springs disposed on the apparatus frame 70 side (see FIG. 1 and FIG. 2) and engaging grooves 24 formed in the rail member 15 of the holder member 11 (see FIG. 2 and FIGS. 6A and 6B). The springs 23 engage the engaging grooves 24 to hold the holder member 11 not to vibrate at the reading position. The springs 23 and the engaging grooves 24 are disposed at four locations on the upper and side portions of the rail members 15a and 15b at the left and right sides, thereby preventing rattle in the vertical and horizontal directions and holding the holder member 11 not to move from the reading position to the setting position through vibrations. A limit sensor 25 (see FIG. 2 and FIG. 3) is disposed on the apparatus frame 70 for detecting the holder member 11 at the reading position. When the holder member 11 is not correctly positioned at the reading position, the limit sensor 25a sends a signal to prevent the scanning operation of the carriage (described below).

Figure 8A:
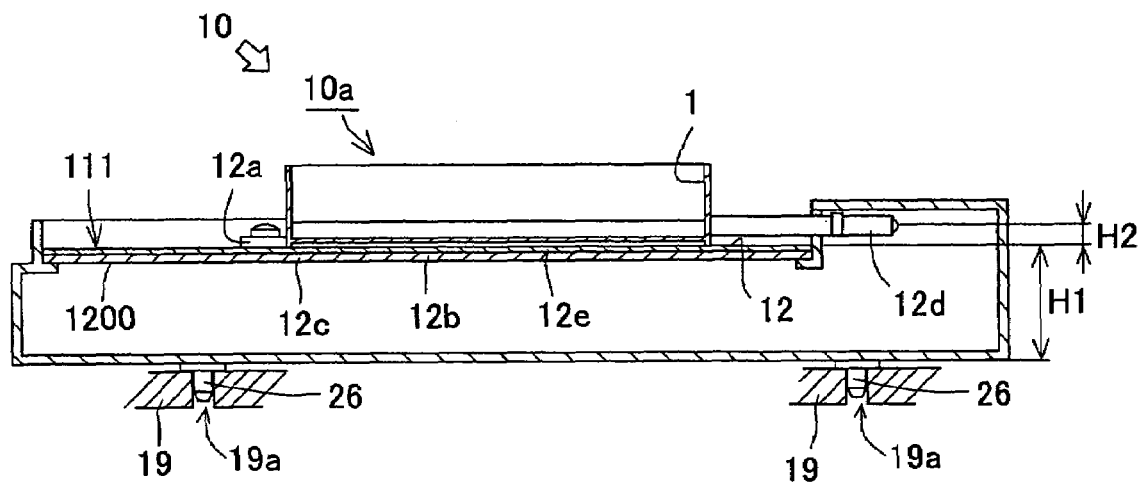
Figure 8B:
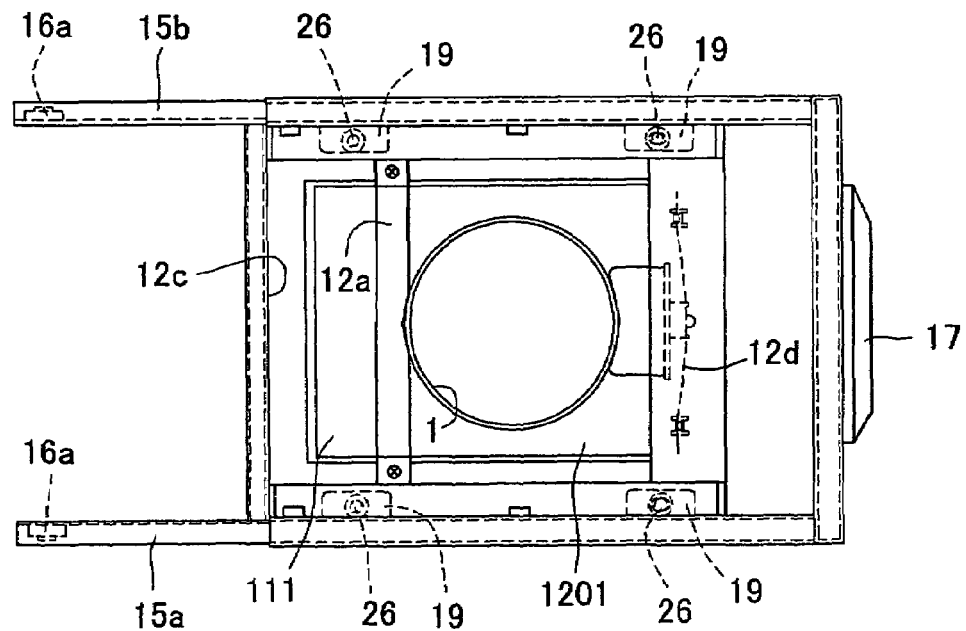

Two stages 10 with the structure described below are detachably installed on the holder member. Each of the stages 10 is provided with the stage surface 12 for setting the specimen and has a shape corresponding to the mounting surfaces 19 of the holder member 11. The stage surfaces 12 are arranged at the focus positions at the predetermined reading position when the specimens are placed thereupon. As shown in FIGS. 8A, 8B and 11, the stage 10a is provided for setting the liquid specimen in a container, and the stage 10b is provided for setting the sheet specimen.

The stage 10a for the transparent specimen shown in FIGS. 8A and 8B will be explained. The stage 10a is provided with a setting plate 1200 for placing a Petri dish containing the liquid specimen such as bacteria, and protrusions 26 (pins) for engaging holes 19a formed in the mounting surfaces 19 of the holder member 11. The setting plate 1200 is mounted on an opening 12c and composed of a transparent glass plate 12e and the diffusion plate 12b such as a frosted glass arranged to overlap with a lower surface of the glass plate 12e. The diffusion plate 12b diffuses light from the transmissive light source 50, and light passes through the glass plate 12e and irradiates the specimen in a Petri dish on a surface (stage surface 12) of the glass plate 12e. A position aligning member 12a for touching and positioning the container such as a Petri dish, and urging means 12d for pressing and holding the container (specimen) at the position aligning member 12a are disposed on the stage surface 12.

As shown in FIG. 8B, the position aligning member 12a is divided the stage surface 12 into two regions: a specimen setting region 1201 for placing the specimen and a transmissive reference region 111 (reading reference region). The transmissive reference region 111 is to attain a reference signal in the transmissive reading mode (described below). The line sensor 32 reads light from the transmissive light source 50 passing through the transmissive reference region 111 to attain the reference signal for the gain adjustment or shading correction.

A transparent material is used for the container such as a Petri dish. The stage surface 12 of the stage 10a is arranged at a mounting height H1 (see FIG. 8A) such that a substantially central area of the specimen matches to the predetermined focus position according to a height H2 of a container 1 and a specimen contained therein (substantially center height of a liquid surface). Specifically, the focus position corresponding to the resolution is set at the height (H1+H2) from the mounting surface 19 of the holder member 11. Note that the height of the specimen in this case is preset and is established as the apparatus specifications.

The protrusions 26 (pins) are formed on a bottom portion of the stage 10a, and have a shape fitting in the engaging holes 19a formed in the mounting surfaces 19 of the holder member 11. Accordingly, the positioning means is formed of the protrusions 26 and the engaging holes 19a. The stage 10 can be installed at a predetermined position when mounting to or removing for replacement from the holder member 11. Note that the protrusions and the engaging holes can be reversed. Specifically, the engaging holes can be formed in the stage 10a, and the protrusions can be formed on the holder member 11 to attain the same positioning effect. Furthermore, the positioning means can be formed of lip surfaces mutually engaging, thereby attaining the same positioning effect.

Figure 10A:
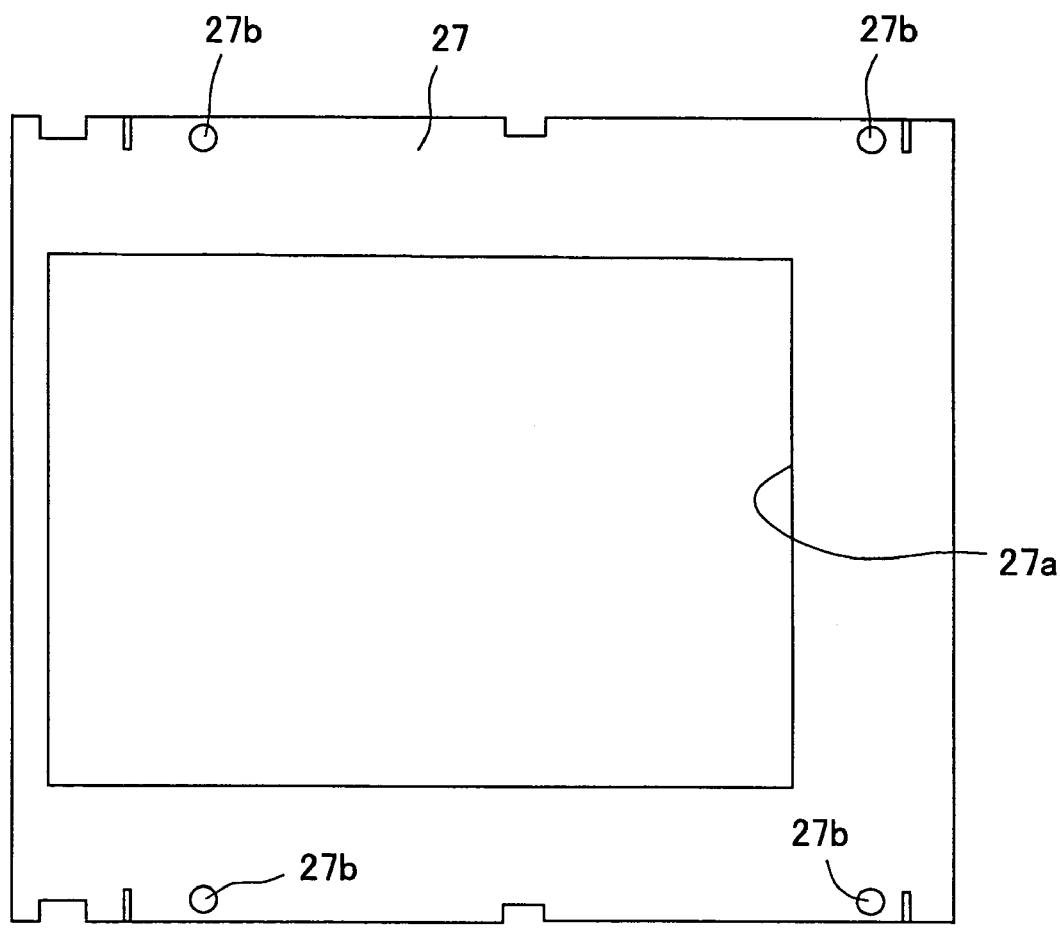
Figure 10B:
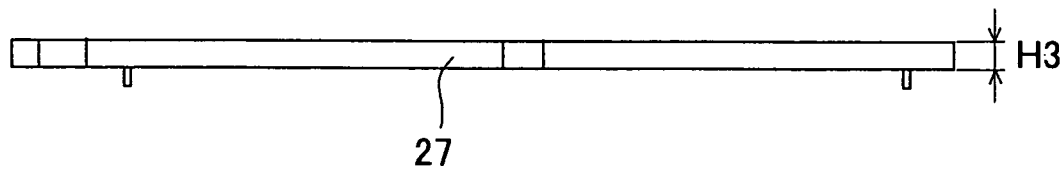

When the reading position (height) for the specimen contained in the container is shifted from the predetermined focus position, it is difficult to obtain correct image data of the specimen. In that case, the height position is adjusted using a height adjustment member 27 shown in FIGS. 10A and 10B. The height adjustment member 27 is formed of a plate member having a thickness H3 (adjusted height). Several height adjustment members 27 with a different thickness (adjusted height) H3 are prepared in advance. The height adjustment member 27 is provided with holes 27b for engaging the protrusions 26 on the stage 10a, and an opening 27a corresponding to the open portion 12c of the stage 10a.

As shown in FIG. 9, the stage 10a engages and is supported on the mounting surface 19 of the holder member 11, and the stage surface 12 is supported at the predetermined height H1 from the mounting surface 19. The container 1 is placed on the stage surface 12, and is positioned with the position aligning member 12a and the urging means 12d. Note that when mounting and dismounting the stage 10a on and from the holder member 11, or when removing or placing the specimen from or on the stage surface, the holder member 11 is moved to the setting position shown in FIG. 1 and FIG. 7.

The stage surface 12 is formed of a transparent glass plate 12e mounted to the open portion 12c. The diffusion plate 12b such as a frosted glass is disposed on a bottom side of the glass plate 12e. Light from the transmissive light source 50 (described below) is diffused by the diffusion plate 12b, thereby irradiating the specimen in the container 1 from the transparent stage surface 12.

A configuration of the stage 10b for placing the opaque specimen such as a sheet will be explained with reference to FIG. 11. The stage 10b is provided with the protrusions 26 and a stage plate 1200 in the same way as the stage 10a. The stage surface 12 on the upper surface of the stage plate 1200 is formed at a predetermined height H4 for placing the sheet to be read. Note that the stage plate 1200 is not limited to a transparent material, and is formed of a glass plate 12e and a diffusion plate 12b in the same way as the stage 10a, so that light can pass therethrough for reading a transparent sheet such as a film. A pushing member 28 is disposed on the stage surface 12 for holding the sheet on the stage surface 12. The pushing member 28 is formed of a glass or another transparent material, and is mounted to the stage surface 12 with a hinge pin 28a. The pushing member 28 presses a sheet on the stage surface to hold with its weight.

In the same way as the stage 10a, the stage surface 12 is divided into two regions, i.e. a specimen setting region 1201 for placing the specimen and a transmissive reference region 111 (reading reference region). In the transmissive reading mode, a reference signal is obtained by reading light from the transmissive light source passing through the transmissive reference region 111.

Figure 12A:
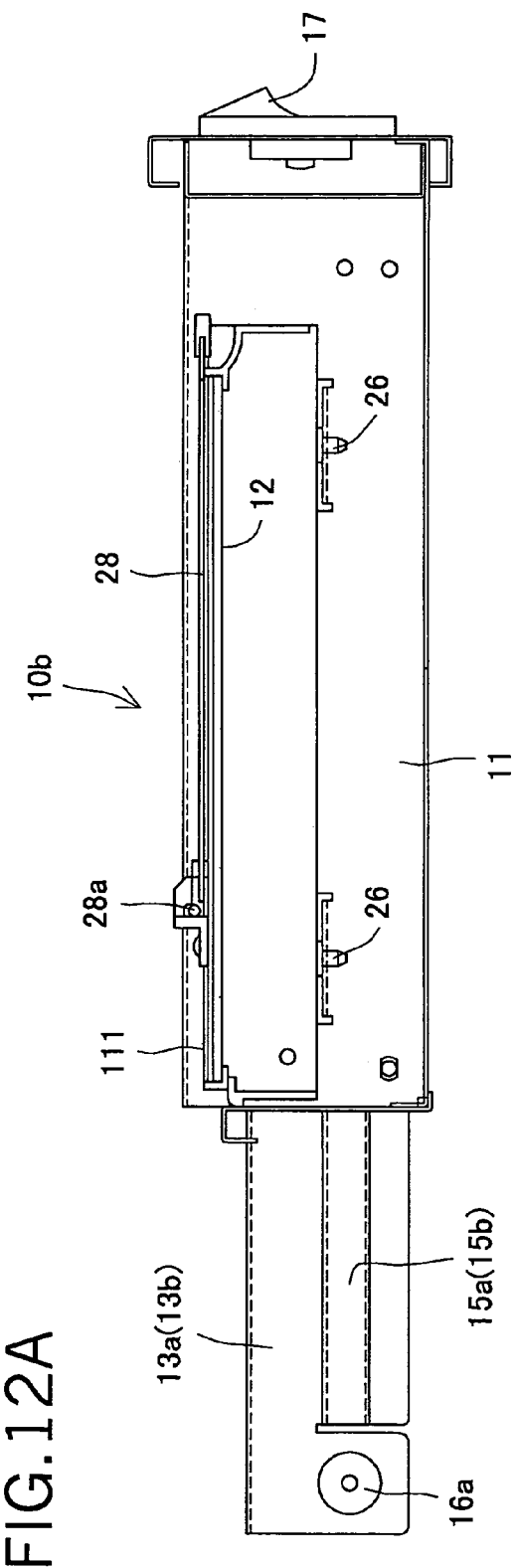
FIG. 12A is a view showing the stage shown in FIG. 11 mounted to a holder member.
Figure 12B:
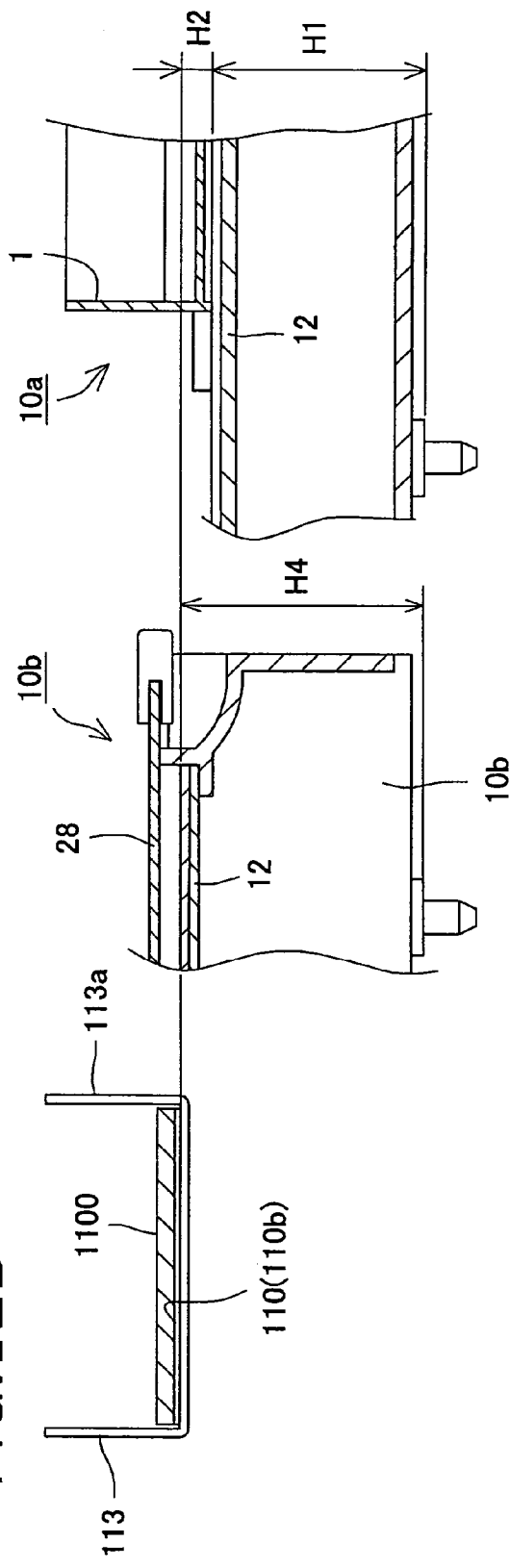
FIG. 12B is a view showing the stage shown in FIGS. 8A, 8B and 9 in a mounted state.

FIG. 12A shows the stage 10b mounted to the holder member 11 on the apparatus frame 70. The mutual relationship with the stage 10a will be described with reference to FIG. 12B. The stage 10b is arranged such that the mounting height H4 (stage surface) matches to the focus position indicated by projected line in FIG. 12B. The stage 10a is arranged such that the mounting height H1 of the stage surface 12 and the height H2 according to a bottom thickness of the containers such as a Petri dish and the thickness of the specimen match to the focus position. That is, the center of the specimen is set at a position according to the height (H1+H2) and a focus depth. In the embodiment, the focus depth is approximately 3 mm, the specification thickness of the sheet specimen is approximately less than 1 mm, and the specification height of the liquid specimen is approximately 2 mm. Therefore, the relationship of the heights shown in FIG. 12B is obtained within variations in the specifications. As shown in FIG. 12B, the reflective reference surface 110 (described below) is positioned at the focus position.

A configuration of the transmissive light source unit C arranged below the stage unit B will be explained next. In the apparatus frame 70, the transmissive light source 50 is arranged below the second guide members 21. The light source 50 is configured to move in synchronization with the carriage 35 (hereinafter referred to as the first carriage 35) in the same direction with the same amount of movement. As shown in FIG. 2, the transmissive light source unit C is provided with the bar shaped light sources 50a and 50b in the direction that the elements of the line sensor 32 are arranged (main scanning direction), and the second carriage 51 mounted with the light sources 50a and 50b. The second carriage 51 is slidably supported by a pair of rod-shaped guide members 52a and 52b. The guide members 52a and 52b (hereinafter referred to as third guide members) are composed of rod members and fastened to the apparatus frame 70 in parallel to the first guide member 36 of the first carriage 35.

The second carrier 51 is formed of a molded plastic like the first carriage 35, and engages an integrated bearing (not shown) to be supported on the third guide members. A second light source composed of a xenon lamp is mounted to the second carriage 51 for irradiating the stage surface 12 of the stage unit B. The two light sources are provided for obtaining light with high intensity since the diffusion plate 12b reduces light and a front surface is irradiated from a back surface of the specimen. The two light sources are provided also for smoothing and evenly irradiating light diffused by the diffusion plate 12b onto the specimen.

A drive motor 90 (described below) is connected to the second carriage 51, so that the second carriage 51 moves reciprocally between the home position represented by solid line and a position indicated by hidden line in FIG. 2. A drive belt 54 is placed between a pair of pulleys 53a and 53b mounted on the apparatus frame 70, and the second carriage 51 is fixed to a part of the drive belt 54. The pulley 53a is connected to the drive motor 90. A glass plate 55 is mounted to an opening for passing light from the second light source 50 toward the stage 10.

Figure 13:
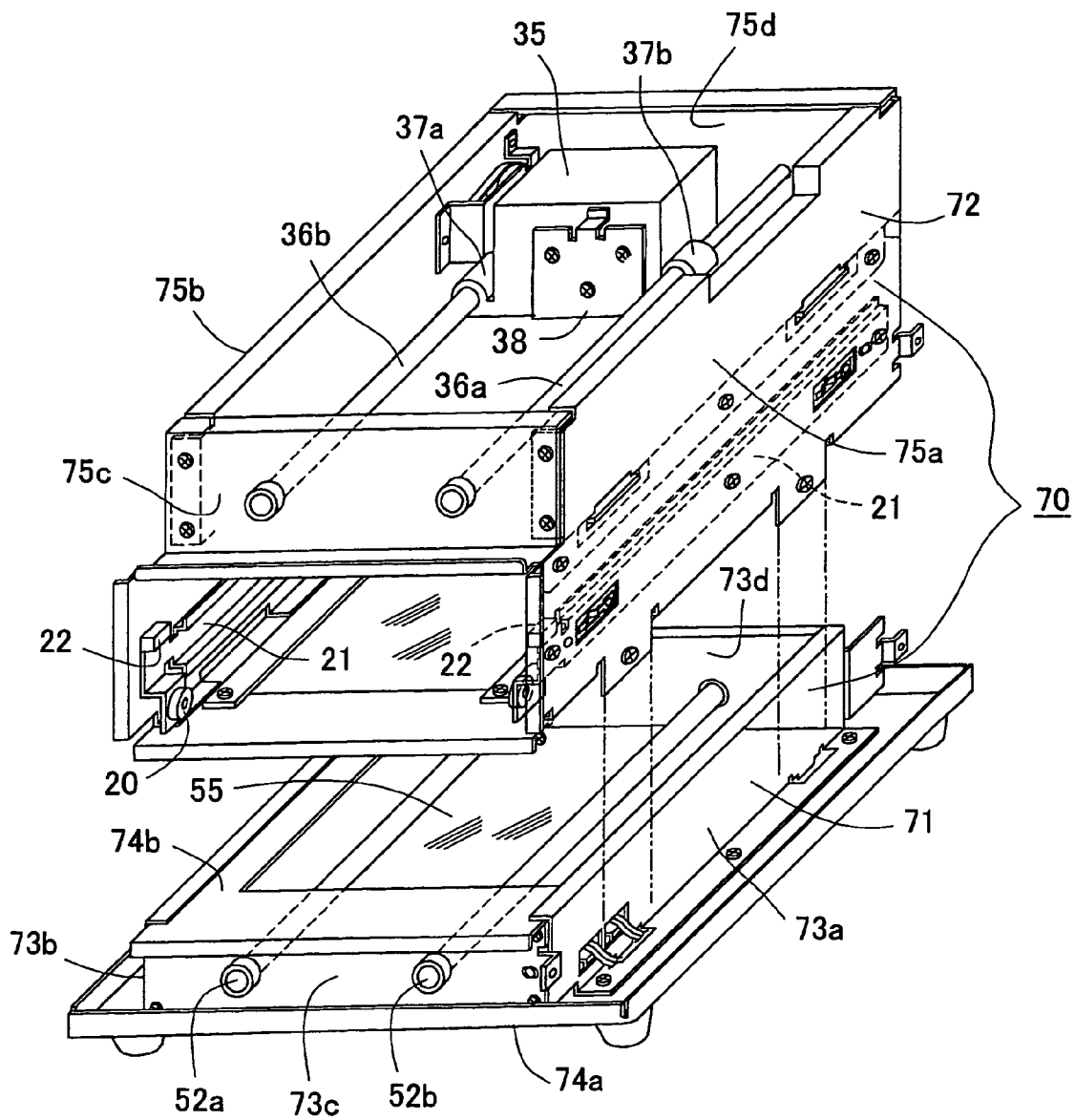
FIG. 13 is an exploded perspective view of a frame structure of the apparatus shown in FIG. 1.

Each of the units described above is assembled into a separate frame. The individual frames are stacked and joined from the bottom to top in the order of the transmissive light source unit, the stage unit, and the scanning unit. In the embodiment, the following structure is employed. FIG. 13 shows the assembly structure of the apparatus frame 70. The apparatus frame 70 is composed of the first frame assembly 71 and the second frame assembly 72 different from the first frame assembly 71. The transmissive light source unit C (second carriage) is assembled into the first frame assembly 71. The stage unit B and the scanning unit A (the first carriage 35) are assembled into the second frame assembly 72.

The third guide members 52a and 52b of the transmissive light source unit C are fastened to the first frame assembly 71. The first frame assembly 71 is formed in a box shape with the four sidewalls 73a, 73b, 73c and 73d, and the bottom plate 74a. Both ends of the third guide members 52a and 52b are supported by the opposing pair of the sidewalls 73c and 73d. The glass plate 55 is mounted to the top plate 74b. The top plate 74b separates the transmissive light source 50 from the open portion 156 for housing the stage unit B arranged above the light sources 50, thereby preventing dirt from entering.

The second frame assembly 72 is formed in a box shape and rigidly assembled into a square shape with the side plates 75a, 75b, 75c, and 75d. An opposing pair of the side plates 75a and 75b (second sidewall) is arranged in the sub-scanning direction (substantially parallel) of the first carriage 35 assembled therein. An opposing pair of the side plates 75c and 75d (first sidewall) is arranged in the main scanning direction (substantially parallel). The side plates 75a and 75b (second sidewall) are arranged in the long direction, and the side plates 75c and 75d (first sidewall) are arranged in the short direction. The second sidewall is set to be longer than the first sidewall. The second guide member 21 of the stage unit B is mounted to the side plates 75a and 75b. The first guide member 36 of the first carriage 35 is mounted to the side plates 75c and 75d. The second guide member 21 is mounted substantially parallel to the side plates 75a and 75b (second sidewall).

Specifically, both ends of the rod members 36a and 36b, i.e. the first guide member 36, are fastened to the opposing side plates 75c and 75d in the short direction. A rail member, i.e. the second guide member 21, is mounted to the opposing side plates 75a and 75b in the long direction. The first guide members 36 and second guide member 21 are mounted to the second frame assembly 72, and the third guide members 52a and 52b are mounted to the first frame assembly 71, so that the positional relationship of the first carriage 35 and the stage 10 is maintained with high precision. Light diffused by the diffusion plate illuminates the specimen, so that the transmissive light source 50 does not require accurate positioning.

The stage unit B and the first carriage unit 35 are assembled into the second frame assembly 72 with great precision when manufacturing the apparatus. In a step separate from the manufacturing process, the transmissive light source unit C is assembled into the first frame assembly 71. When the second frame assembly 72 is arranged over the first frame assembly 71, and the second frame assembly 72 is fastened to the first frame assembly 71 using screws, it is possible to manufacture a simple apparatus with low cost. The first and second guide members are assembled to the second frame assembly 72 as described above. As shown in FIG. 2, the glass plate 76 is disposed between the first carriage 35 and the stage unit B in the following way.

As shown in FIG. 2, a separation plate 77 (cover member) is fastened to the side plate constituting the second frame assembly 72, so that the box-shaped frame assembly 72 is divided into the housing space (moving region) 1300 of the first carriage 35 and the open portion 156 for housing the stage unit B. Accordingly, it is possible to prevent the optical system 30 or the line sensor 32 from becoming dirty by dust from outside of the first carriage 35 or scattered liquid specimen such as bacteria. The glass plate 76 is mounted to the separation plate 77. Therefore, the apparatus housing is divided into the first carriage storage space, the stage storage space, and the transmissive unit storage space for the first and second frame assemblies by the glass plate 76 of the separation plate 77 and the glass plate 55 of the transmissive light source unit C.

As shown in FIG. 2 and FIG. 3, the open portion 156 is divided by the separation plate 77 and the upper plate 74b. The holder member 11 mounted with the stage 10a or the stage 10b is housed in the open portion. The bracket 113 mounted with the reflective reference plate 110 (described below) protrudes into the open portion 156 and is mounted with the separation plate 77. The reflective reference plate 110 and the reflective reference surface 110b are positioned in the open portion 156.

The reflective preference plate for obtaining the reference signal for reading in the reflective reading mode is incorporated into the apparatus as described below. The reflective reference plate 110 (first reading reference plate) is disposed on the apparatus frame 70 at a position away from the stage 10 (second frame assembly 72 in the embodiment).

Figure 14:
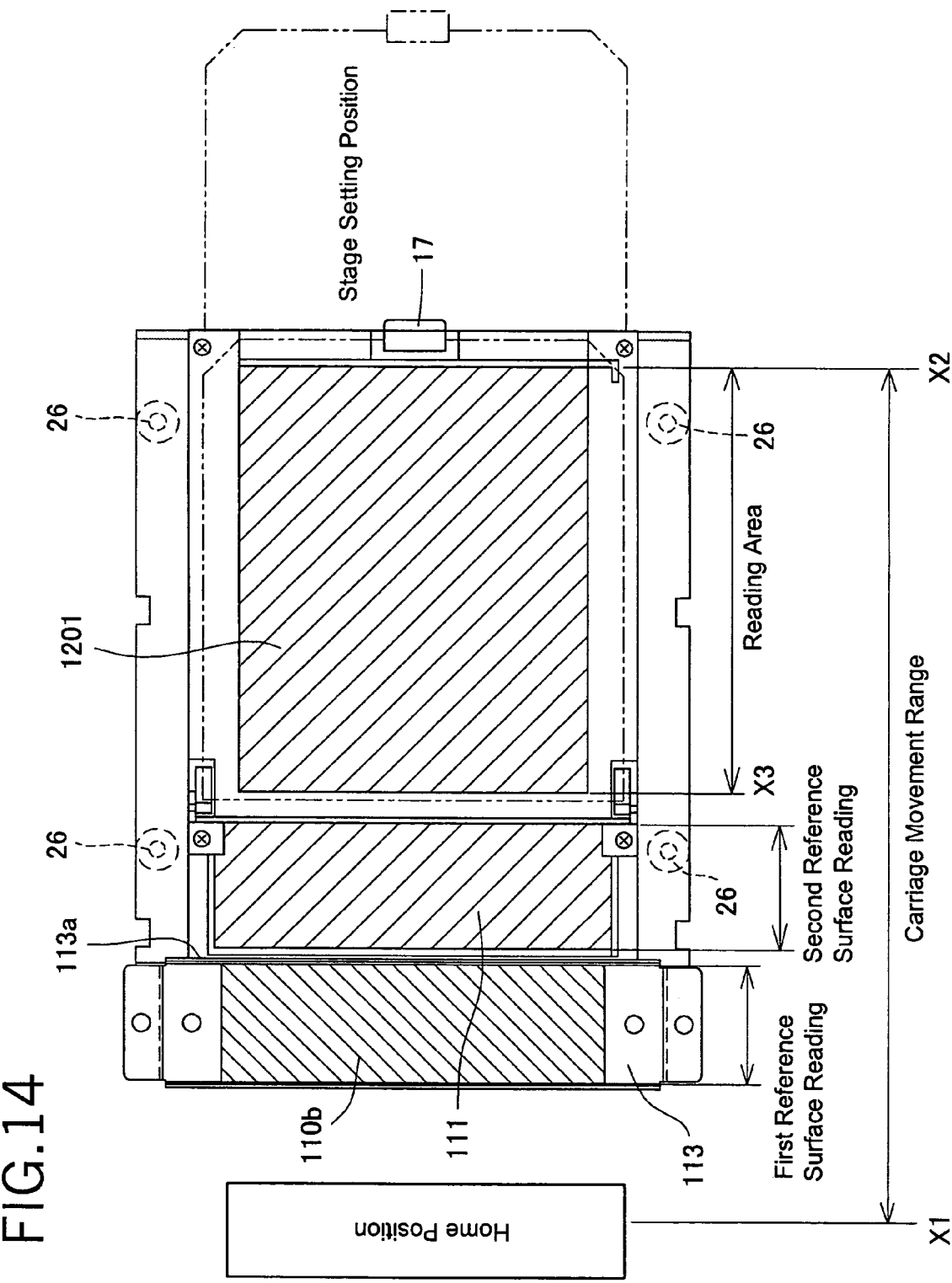
FIG. 14 is a sectional view taken along line 14-14 in FIG. 3 showing a positional relationship of each region.

A positional relationship of each of the members when the holder member 11 mounted with the stage 10b is set at the reading position will be explained in reference to FIG. 14, i.e. a sectional view taken along line 14-14 in FIG. 3. As shown in FIG. 14, arrows at x1 and x2 indicate directions of the movement of the first carrier 35. In the drawing, x1 on the left side is the home position of the carriage 35; x2 is the reading end position; and x3 is the reading start position. From the home position x1 of the carriage 35 to the reading end position x2, these are arranged in the order of the reflective reference 110, the transmissive reference region 111, and the specimen stage region 1201.

As shown in FIG. 3, the reflective reference plate 110 is disposed on the bracket 113 having a U-shape section. The bracket 113 is mounted to the separation plate 77 mounted to the apparatus frame 70. The reflective reference plate 110 is formed of a white film material (opaque-matertial). The film material is attached to the bottom surface of the glass plate 1100, and the glass plate 1100 is fastened to the bottom portion of the bracket 113. The bracket 113 is formed of a channel member and disposed on the bottom side of the glass plate 76 mounted to the separation plate 77. As shown in FIG. 12B, the reflective reference surface 110b on the top surface (front surface) of the reflective reference plate 110 is positioned at the predetermined focus position indicated by hidden line above the stage surface 12 of the stage 10a. As shown in FIG. 3, the reflective reference surface 110b is positioned below the carriage 35.

According to the embodiment, the reflective reference plate 110 is formed on the bottom surface of the glass plate 1100. In the reflective mode (described below) for reading light reflected from the first light source 31, the specimens are mainly formed in sheets. The glass holding member 28 described above is provided on the stage 10b for the sheet specimen, and the holding member 28 is placed on the sheet for reading. In order to read the reflective reference plate 110 under conditions nearly same as those for the sheet, the reflective reference plate 110 is formed on the bottom surface of the glass plate 1100. When the stage 10b is not provided with the holder member 28, a white film is attached to the bottom surface of the bracket 113 as the reflective reference surface 110.

The reflective reference plate 110 (reflective reference surface 110b) is surrounded by the bracket 113 to prevent dust from entering. In particular, the sidewall 113a of the bracket 113 is disposed adjacent to the stage surface 12 for preventing a liquid specimen from scattering. The bracket 113 is suspended and supported from the separation plate 77 of the apparatus frame 70 arranged with the first carriage 35. Accordingly, a side portion of the apparatus frame 70 is used as a layout space for a movement mechanism of the stage 10 such as the first guide member 36, thereby making the apparatus compact.

As shown in FIGS. 8A, 8B, and 11, the reflective reference surface 10b is mounted on the apparatus frame 70 away from the stage 10. Alternatively, the reflective reference surface 10b and the transparent transmissive reference region 111 may be mounted to the stage 10 as shown in FIG. 12B, in which the stage 10 is mounted to the holder member 11. Similar to the stage 10a and 10b, the stage 10 is provided with the stage surface 12 formed of a glass plate and the diffusion plate 12b disposed below the stage surface 12. The stage surface 12 of the stage 10 includes a specimen setting region 1201, transmissive reference region 111b, and reflective reference surface 110a for the reflective reading mode arranged in this order. Specifically, the reflective reference surface 110a, the transparent reference region 111b, and the specimen the setting region 1200 are arranged in this order from the home position of the first carriage 35. The reflective reference surface (region) 110a is formed of an opaque white film attached to the stage surface 12, and a glass plate may be disposed over the film if required. Each reference surface (region) is arranged on the stage configured to be detachable from the apparatus frame. Accordingly, it is easy to clean the surfaces when become dirty with dust.

Figure 5:
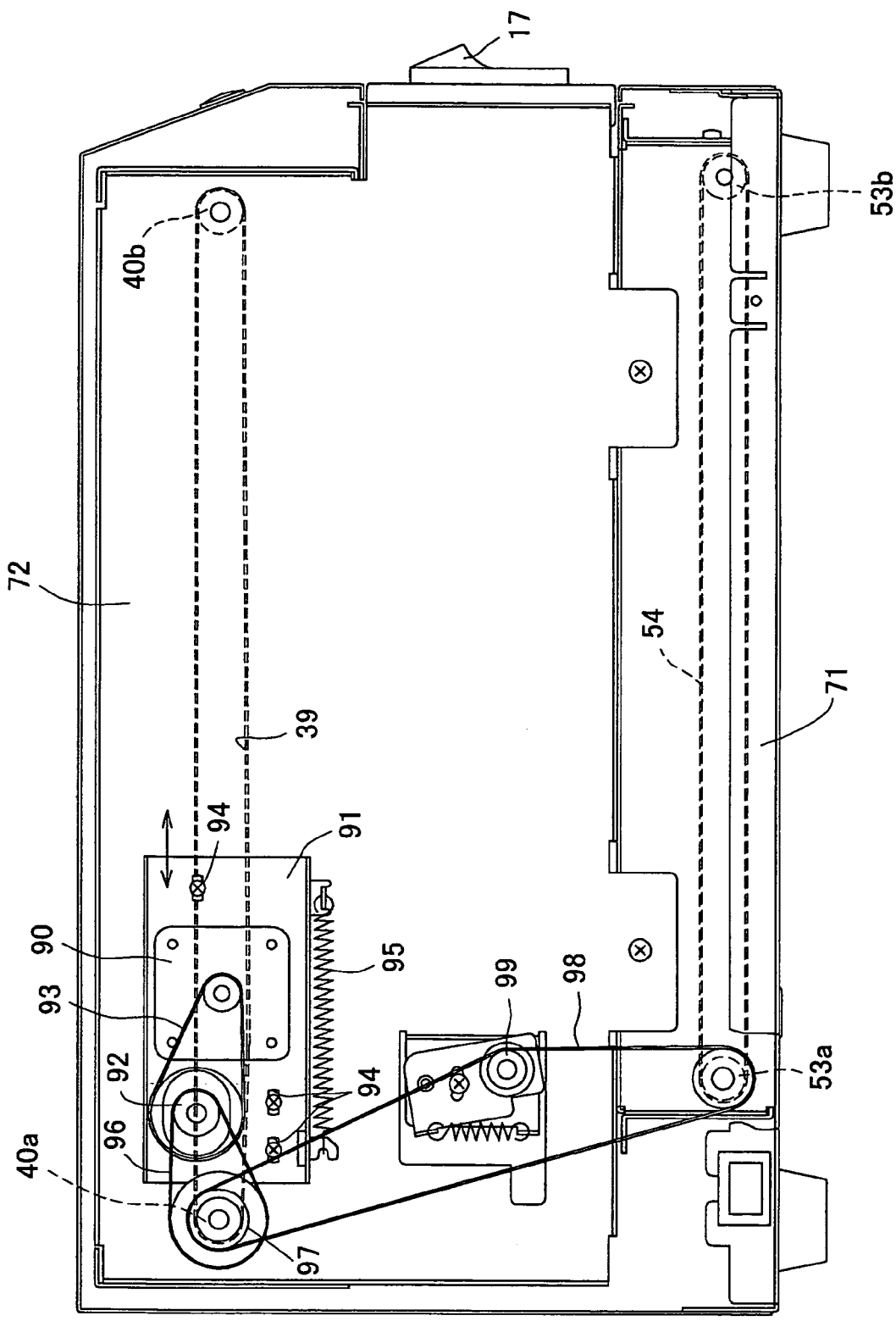
FIG. 5 is a view showing a drive mechanism in the image reading apparatus shown in FIG. 1.

The first carriage 35 having the optical system 30 and the line sensor 32 and the second carriage 51 of the transmissive light source unit C are connected to the single drive motor 90. The drive motor 90 is a stepping motor capable of both forward and reverse rotations. As shown in FIG. 5, the drive motor 90 is mounted to the second frame assembly 72 of the apparatus frame 70. The motor 90 is fastened to the motor bracket 91 mounted with the transmission pulley 92. The transmission pulley 92 and motor rotating shaft are connected by a transmission belt 93. The transmission pulley 92 and the pulley 40a of the drive belt 39 are connected by the transmission belt 96.

The motor bracket 91 is adjustably supported on a long groove in the sidewall 73a of the apparatus from 70 to be movable in the left and right directions. The bracket 91 is urged to the right side in FIG. 5 by a spring with one side attached to the sidewall 73a for adjusting tension of the transmission belts 93 and 96. In this way, the pulley 97 mounted to the same shaft as the pulley 40a receiving the rotation of the drive motor 90 and the pulley 53a of the second carriage 51 are connected by the transmission belt 98. A tension roller 99 is urged by an urging spring to adjust tension of the transmission belt 98. Therefore, the first carriage 35 and the second carriage 51 reciprocally move simultaneously with the same amount in the same direction (sub scanning direction) through the forward or reverse rotation of the drive motor.

Figure 15:
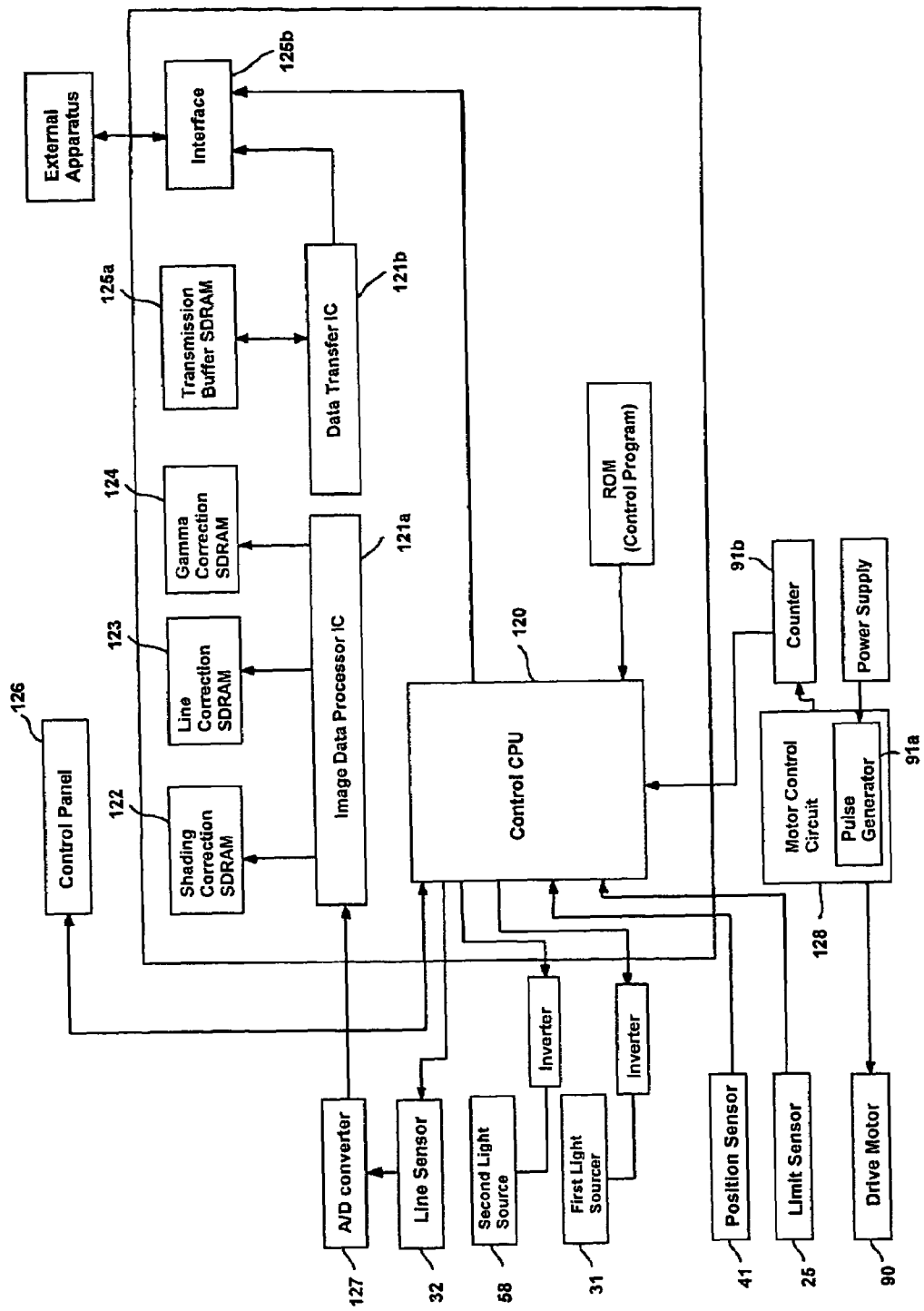
FIG. 15 is a block diagram of a control circuit of the image reading apparatus shown in FIG. 1.

A control of the apparatus will be explained with reference to FIG. 15. After the line sensor 32 reads the specimen on the stage 10 and the image data is processed and converted into digital information, the data is output to an external apparatus such as a computer or printer. The digital image data undergoes necessary processing on an external apparatus to be analyzed on the computer or printed onto a paper.

A control circuit is installed in the apparatus described above. In the embodiment, a control CPU 120, an image data processor IC 121a, and a data transfer IC 121b are mounted on a control substrate attached to the side plate 75b of the apparatus frame 70. A shading correction SRAM 122, line space correction SRAM 123, and gamma correction SRAM 124 are connected to the image processor IC 121a. A buffer SRAM 125a and interface 125b for sending data to an external apparatus are connected to the data transfer IC 121b. A control circuit 128 of the drive motor 90 is connected to the control CPU 120. A position sensor 41 for the first carriage 35 and a limit sensor 25 for the stage unit B are connected to the control CPU 120 for transmitting a detection signal. A control panel 126 is used for turning on the apparatus and setting various image reading conditions. A command line is also established in the control CPU 120 for setting the image reading conditions from an external apparatus.

The first and second light sources are connected to power supplies via an inverter and the control CPU 120. The power supply to the reflective light source 31 (first light source) and the power supply to the transmissive flight source 50 (second light source) are controlled to turn on and off by the CPU 120. The control CPU 120 is connected to a control circuit of the line sensor 32 to send a synchronizing signal (clock signal) to the line sensor 32, so that start up power is sequentially transferred to each of the configuring elements. The electrical signal output from the line sensor 32 is converted into the digital signal by the A/D converter 127 then transferred to the image data processor IC 121a.

A pulse generator circuit 91 for supplying a pulse voltage to the motor (stepping motor) and a counter 91b for counting the pulse are provided on the control circuit 128 of the drive motor 90. The counter 91b is connected to the control CPU 120. The control CPU 120 controls the amount of rotation of the drive motor 90 using the pulse count of the supply voltage to control the positions of the first carriage 35 and the second carriage 51. The limit sensor 25 is connected to the control CPU 121 for detecting the holder member 11 to monitor whether the stage is positioned at the predetermined scanning (reading) position. It is possible to determine whether the first carriage 35 is at the home position using a signal from the home position sensor 41.

An operation of the image reading apparatus according to the present invention will be explained next with reference to FIG. 16A and FIG. 16B. The apparatus sets the scanning speeds (movement) of the first carriage 35 and the second carriage 51 synchronized thereto according to an operating mode (for example, a reading condition such as a type of image (color, black and white, or gray scale)) and resolution. The reading conditions can be set either from an external apparatus or using the control panel. It is possible to configure the external apparatus to set a reading range of the specimen (trimming setting). In this case, the specimen is pre-scanned once to set a range (trimming) using a display apparatus such as a CRT, to read the specified range under the set conditions.

FIG. 16A is a flow chart showing an initial operation of the apparatus. FIG. 16B is a flowchart showing an operation of reading an image. In FIG. 16A, the initial operation is executed when the apparatus is turned on. When the power to the apparatus is turned on using the control panel (ST1), the control CPU 120 monitors the status of the limit sensor 25 of the holder member 11 and determines whether it is at the reading position (ST2). If the holder member 11 (stage 10) is not positioned at the predetermined reading position (NO in the drawing), a warning is generated in the control panel and the limit sensor 25 idles until the ON signal is received. If the holder member 11 (stage 10) is positioned at the predetermined reading position (YES in the drawing), the control CPU 120 starts the initial process. It is judged by the signal from the position sensor 41 whether the carriage 35 is at the home position when starting the initial process. If it is not positioned at the home position, the CPU 120 rotates the drive motor 90 in the left direction in FIG. 5 to move the carriage 35 to the home position.

Next, the control CPU 120 sends the start signal to the drive motor 90 to move the first carriage 35 to the predetermined position over the reflective reference surface 110b (ST3), then it stops the motor 90. The predetermined position over the reflective reference surface 110b is the position where light from the first light source 31 is interrupted by the bracket 113 supporting the reflective reference surface 110b and is generally the center of the sub scanning direction of the reflective reference surface 110b. The amount of movement of the first carriage 35 is controlled by counting the number of pulses of the pulse voltage of the drive motor by the counter. After the carriage 35 moves to the predetermined position over the reflective reference surface 110b, the control CPU 120 loads the output data of the line sensor 32 while the first and the second light sources 31 and 50 are turned off to find the offset value to adjust the offset.

Note that the offset adjustment is to find an adjustment value (offset value), so that a voltage (dark voltage) for each pixel output from each photoelectric conversion element when the light sources are turned off becomes equal to the lowest input voltage of the A/D converter 127.

Next, when the line sensor 32 is positioned at the predetermined position over the reflective reference surface 110b, the control CPU 120 generates a signal (ST5) to turn on the reflective light source 31 (first light source) to execute the gain adjustment described above while the lamp is on (ST5). Note that the gain adjustment are to find an adjustment value (gain value), so that the voltage for each pixel output from each photo-conversion element based on the reflected light from the reflective reference surface 110b becomes a value close to the maximum input value of the A/D converter when the light sources are on. If necessary, the control CPU 120 repeats the offset adjustment and the gain adjustment, and stops both adjustments when the appropriate offset value and gain value are obtained. Then, the reflective light source 31 is turned off (ST6).

Next, the CPU 120 starts the drive motor 90, and moves the first carriage 35 to the predetermined position over the transmissive reference region 111 (ST7). There, the control CPU 120 stops the first carriage 35 at the position and obtains output data of the line sensor 32 while the first and second light sources are turned off to execute the offset adjustment (ST8). After that, the control CPU 120 turns on the transmissive light source (second light source) and uses the line sensor 32 to read one line of the transmissive reference region 111 to adjust the gain (ST9). At this time, the first light source 31 (reflective light source) is turned off. If necessary, the control CPU 120 repeats the offset adjustment and the gain adjustment, and stops both adjustments when the appropriate offset value and gain value are obtained. Then, the transmissive light source 50 is turned off (ST10). Note that each of the offset values and the gain values for the reflective reading mode and the transmissive reading mode obtained at each of the steps is stored in a memory. Next, the control CPU 120 issues a recovery instruction signal to the drive motor 90. Upon receiving the signal, the drive motor 90 rotates in reverse to return the first carriage 35 to the home position (ST11). Then, the position sensor 41 detects the first carriage 35, and the drive motor is stopped (ST12) after a predetermined pulse count to complete the initial operation (ST13).

A reading operation will be explained with reference to FIG. 16B. First, an operator selects one of a plurality of stages according to a type of specimen to be read with the apparatus. Then, the operator mounts the selected stage 10 onto the holder member 11. To mount the stage 10, the holder member 11 is moved out to the setting position from the apparatus frame 70 (see FIG. 7). The operator sets the specimen on the stage surface 12 at the setting position, and moves the stage 10 to the reading position along with the holder member 11.

At this point, the operator inputs the reading conditions such as (1) image type (color or black-and-white), (2) resolution (in the embodiment, 600/300 dpi), (3) light source selection (reflective light source or transmissive light source), and (4) reading range (ST20) using an external apparatus such as a computer. The operator sets the reading conditions then turns on the start switch. At this point, the control CPU 120 monitors the status of the limit sensor 25 of the stage unit B. If the stage 10 is not positioned at the reading position (sensor signal is off), it idles until the limit sensor 25 turns on. On the other hand, if the limit sensor 25 is on, the CPU 120 executes the black shading process (ST22). The signals from the line sensor 32 are processed while all light sources are turned off at the home position, so that the reference value of the shading correction is set and stored in the memory.

Next, the control CPU 120 judges whether the light used at the initial condition is the reflective light source 31 or the transmissive light source 50 (reflective reading mode or the transmissive reading mode) (ST23), and then the specified light source is turned on (ST24). After that, the control CPU 120 sends the start instruction signal to the drive motor 90 to advance the first carriage 35. Note that the first carriage 35 advances in the order of the reflective reference surface 110b (described below), the transmissive reference region 111, and the reading region (specimen setting region 1201). When the light source to be used is the reflective light source 31, the control CPU 120 advances the first carriage 35 to the reflective reference surface 110b. When the light source is the transmissive light source 50, the control CPU 120 advances the first carriage 35 to the transmissive reference region 111 and executes the white shading process (ST26). This process drives the line sensor while the light source is turned on to acquire data. The variations in the light amount from this data are stored in the memory as correction values for correcting with the image processing. When the first carriage 35 arrives at the predetermined reading starting position, the control CPU 120 sequentially reads the image of the specimen using the line sensor 32 (ST27).

As the control CPU 120 sequentially reads the image by each line, it sequentially transfers the image signal to the memory such as a shift register. After converting the analog signal output from the line sensor 32 into the digital signal by the A/D converter, the image processing IC performs the gain adjustment and offset adjustment using the gain values and offset values described above, the shading correction, line space correction, gamma correction and dither correction. Then, this is transferred to an external apparatus as image data via an interface.

Next, the control CPU 120 judges whether the line count is equivalent to the reading region specified under the initial condition setting (ST28). If the set line count is not reached, it continues reading the next lines. A counter counts the number of main scans for the line count. This is used to compare with the reference values converted to the set reading region base on the resolution for judgment. When the read line count reaches the predetermined line count, the control CPU 120 turns off the light source 31 or the light source 50, and rotates the drive motor 90 in reverse to return the first carriage 35 to the home position to complete the reading operation. Note that in the event the holder member 11 is moved from the reading position during the reading operation, and the limit sensor 25 is detected to be off, the control CPU 120 immediately turns off the light source and returns the first carriage 35 to the home position. Any image data acquired to that point is then discarded.

As described above, the stage 10 for holding the specimen is detachably supported on the mounting surface 19 of the holder member 11. Two or more of the stages 10 can be mounted to the mounting surface 19 of the apparatus frame 70, so that the stage 10 with an optimum characteristic for a material such as a shape of the specimen and transparent or opaque is mounted to the mounting surface 19 of the apparatus frame 70. Therefore, an operator can select and use the stage 10 from a plurality of the stages, so that the reading position of the specimen placed on the stage surface 12 matches to the predetermined focus position.

Second Embodiment

Hereunder, another embodiment of the present invention will be explained with reference to the accompanied drawings.

Figure 17:
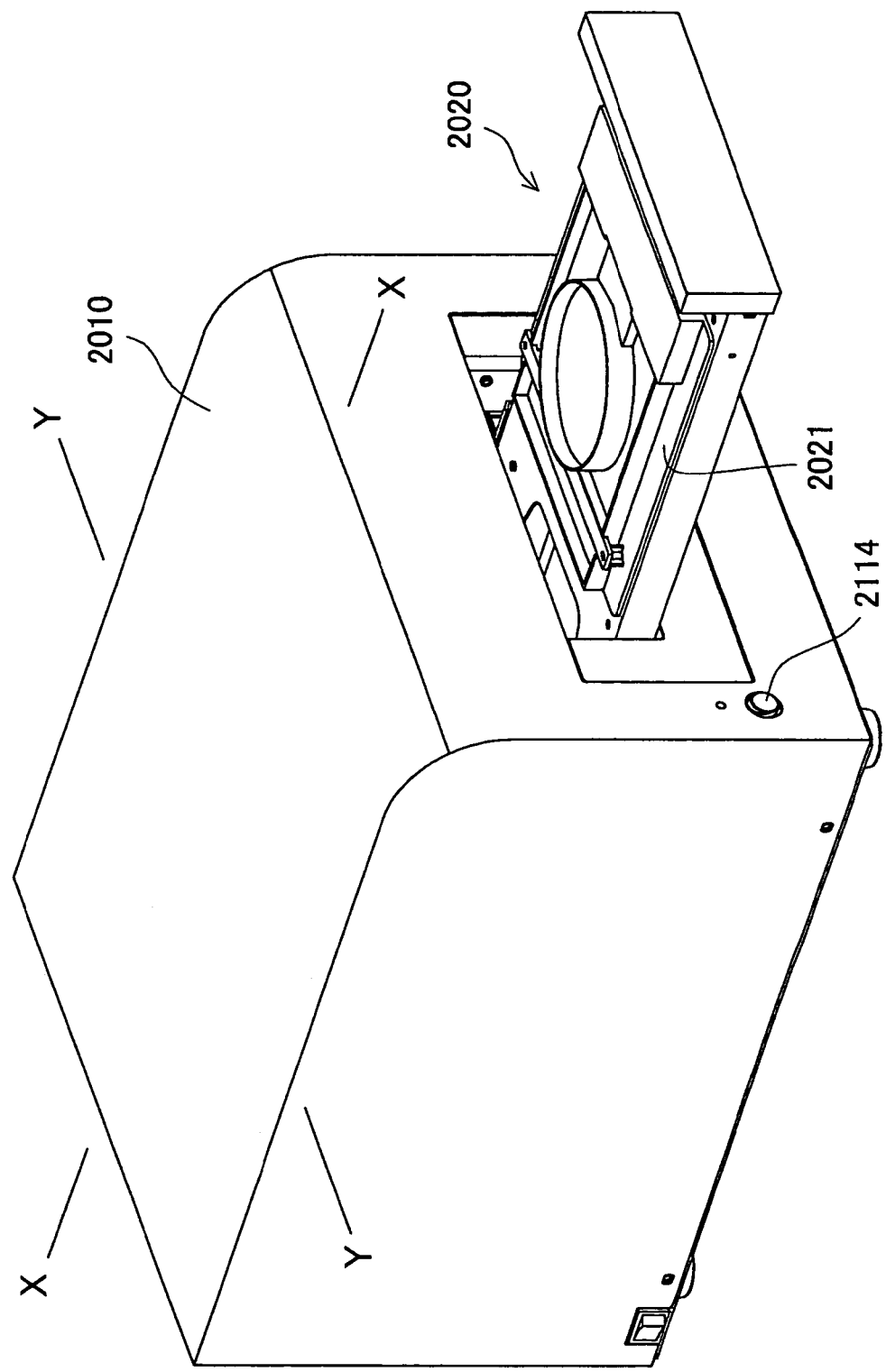
FIG. 17 is a perspective view of an external appearance of an image reading apparatus according to a second embodiment of the present invention.
Figure 18:
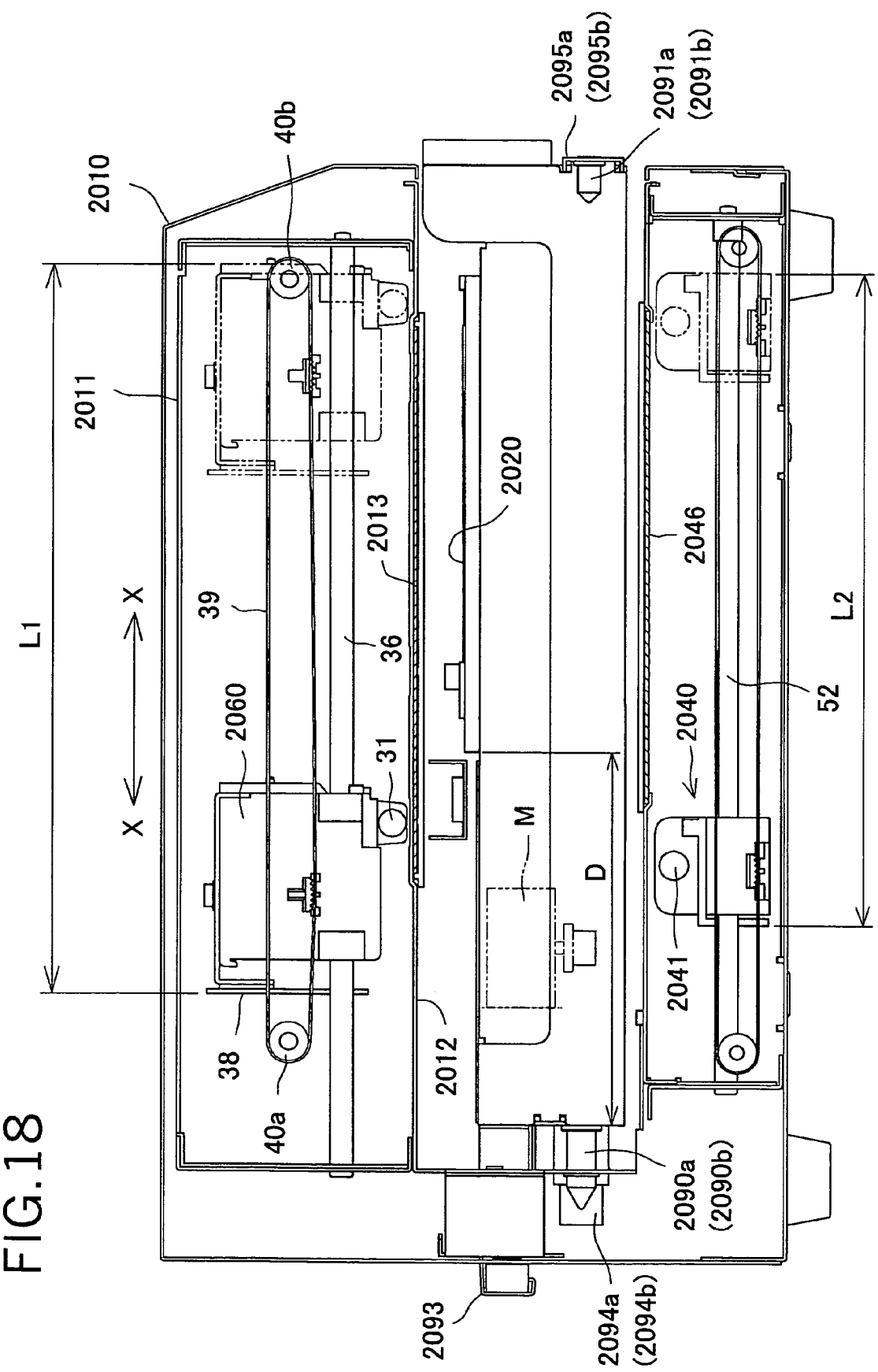
FIG. 18 is a longitudinal sectional view of a central portion of the image reading apparatus shown in FIG. 17.
Figure 20:
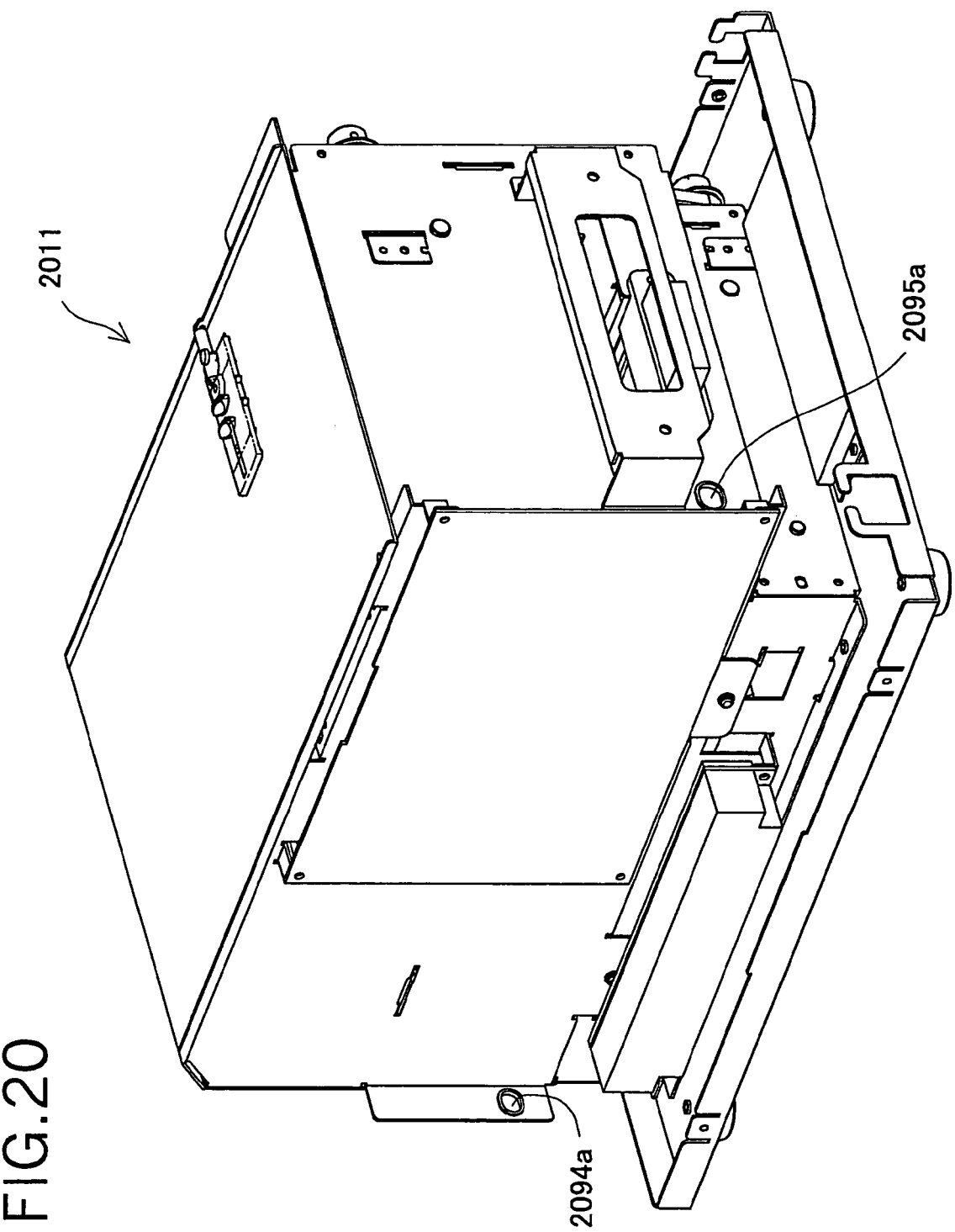
FIG. 20 is a perspective view of an apparatus frame according to the second embodiment of the present invention.

FIG. 17 is a perspective view of the external appearance of the image reading apparatus. FIG. 18 is a view of the structural layout of the internal structure of the apparatus. FIG. 20 is a perspective view of the apparatus frame. Note that FIG. 17 shows a stage (stage 2021) positioned at the setting position outside the apparatus, and FIG. 18 shows the stage positioned at the reading position inside the apparatus.

Also, as can be seen in FIG. 17, a switch 2114 (push switch) is mounted to the front of the apparatus to open and close the stage (to move the stage between the setting position and the reading position). The stage unit 2020 that sets the specimen (hereinafter referred to as the sample) inside the appropriately shaped casing 2010, the light source carriage 2040 (the second carriage) that irradiates light upon the sample on the stage unit 2020, and the scanning carriage 2060 (the first carriage) that reads the light from the sample are incorporated in the image reading apparatus. The reflective light source 31 (the first light source) mounted on the scanning carriage 2060, or the transmissive light source 2041 (the second light source) mounted on the light source carriage 2040 irradiates light on the sample that is set on the stage unit 2020. That reflected light or transmitted light forms an image on the line sensor of the photoelectric conversion means using the optical means such as the mirror and lens. Image information from the line sensor is then electrical output.

The apparatus frame 2011 which is substantially box shaped is incorporated in the casing 2010 as shown in FIG. 20. The scanning carriage 2060 is incorporated in the upper level space of the apparatus frame 2011. In the middle area, the stage unit 2020 is incorporated; and in the lower area light source carriage 2040 is incorporated (See FIG. 18).

The scanning carriage 2060 is mounted with the first light source 31, the optical system (mirrors 33a, 33b, 33c, and 33d, and image forming lines 34) and the line sensor 32 (photoelectric conversion means) that is fastened to the substrate 38.

Note that each of the members mounted on the scanning carriage 2060 have the same number as applied to those in the description in the first embodiments and thus detailed descriptions thereof are omitted.

The scanning carriage 2060 is movably mounted to the apparatus frame 2011 in the X-X direction shown in the drawing that is orthogonal to the array direction (back to front direction of FIG. 19) of the line sensor. As described above, the apparatus frame 2011 is configured into a box shape. Carriage guide members 36 (hereinafter referred to as the first guide members) that are composed of two parallel guide shafts are arranged in the X-X direction in the drawing in the upper space of the apparatus frame 2011. The scanning carriage 2060 is supported on bearings and movably mounted to the first guide members.

The drive belt 39 is trained between the pair of pulleys 40a and 40b and mounted in parallel to the first guide members 36 on the apparatus frame 2011. This drive belt is interlocked to the scanning carriage 2060. The scanning carriage 2060 can thus reciprocally move between solid line of FIG. 18 (home position) and hidden lines by this drive belt 39. Note that the drive transmission system of the scanning carriage 2060 is the same as the one described for the first embodiment and thus a detailed description thereof is omitted.

Thus, as described above, the scanning carriage 2060 is arranged to move reciprocally in the upper space of the apparatus frame 2011, and the dust cover plate 2012 is established on the lower side of the scanning carriage 2060 in this apparatus frame 2011. This prevents dust from entering the scanning carriage 2060 from the stage unit 2020 side, which is described in further detail below. Also, a portion of the dust cover plate 2012 is configured by a transparent glass 2013 to allow light to pass therethrough.

The following shall describe the stage unit 2020 using FIG. 21 to FIG. 25. The stage unit 2020 is mounted to the middle area of the apparatus frame 2011 with the following structure. First, the stage unit 2020 is configured of the stage 2021 (see FIG. 25) that sets samples; the stage support means 2022 (hereinafter referred to as the sliding member 2022) that holds the stage 2021; and the stage guide 2023 (the second guide member) that sliding supports the sliding member. The stage unit 2020 is embedded in the apparatus frame 2011. The stage guide 2023 supports and guides the stage 2021 (sliding member 2022) to enable it to move in substantially the same direction as the direction of movement of the scanning carriage 2060. This is to position the stage 2021 which is mounted to the sliding member 2022 at a predetermined position (reading position) inside the apparatus frame 2011 and the setting position outside of the apparatus frame 2011.

Still further, a bottom plate 2025*c* is mounted to the stage unit 2020. The diffusion plate 2204 formed of an acrylic plate is mounted to the opening of this bottom plate 2025*c*. This is to illuminate light (transmissive light) onto the sample that is on the stage 2021 which is positioned at the reading position by diffusing light from the light source carriage 2024, which is described in further detail below. Note that according to the embodiment, the diffusion plate 2004 is fastened to the bottom plate 2025*c* by screws. However, it is perfectly acceptable to provide waterproofing treatment such as fitting a sealing material between the bottom plate 2025*c* and the diffusion plate 2204 to prevent a run out of the sample, if a liquid sample spills. Still further, by unitizing the bottom plate 2025*c* and the diffusion plate 2204, a waterproofing effect is attained without using a sealing material.

Figure 23:
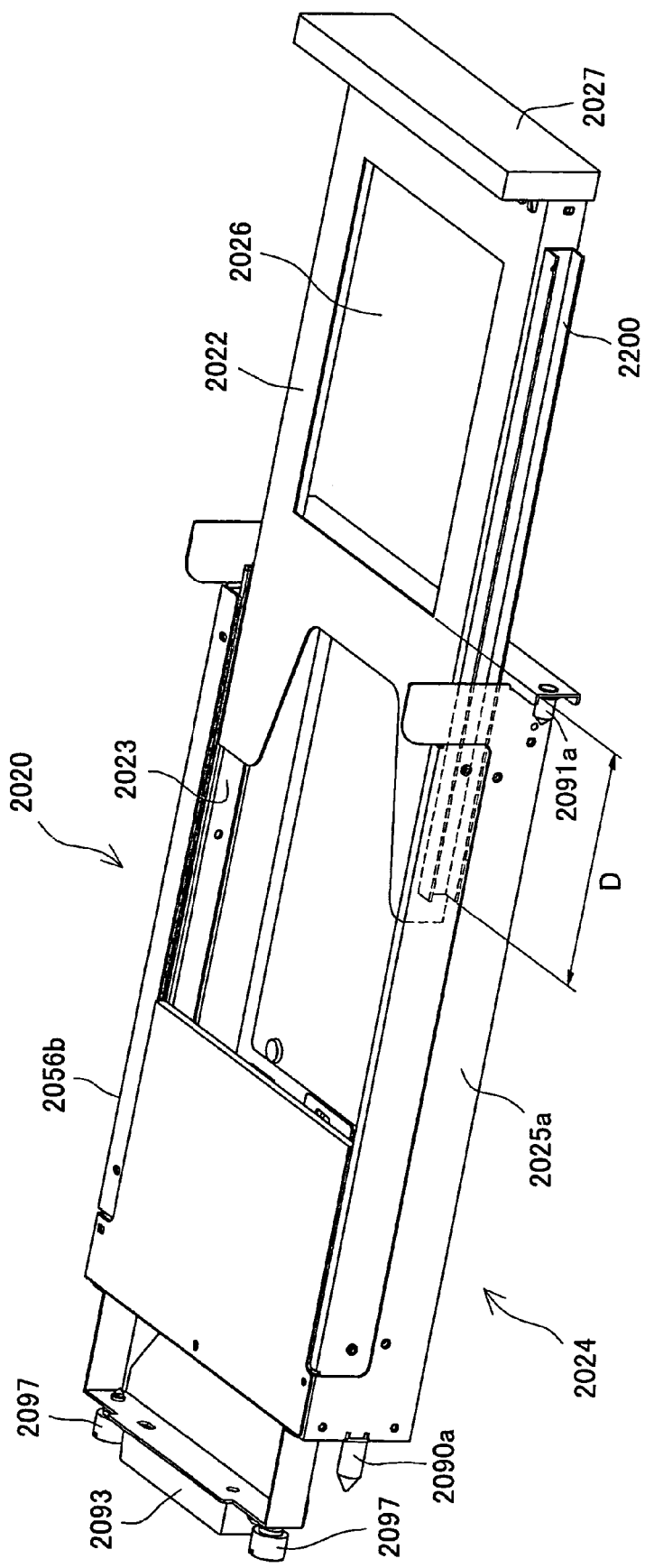
FIG. 23 is an overall perspective view of the stage unit according to the second embodiment of the present invention.

As shown by the overall perspective view of FIG. 23, the stage unit 2020 comprises a substantially box-shaped unit frame 2024. This unit frame 2024 is fastened to the apparatus frame 2011. A stage guide 2023 (second guide member, hereinafter referred to as the guide rails) which is composed of a pair of guide rails is arranged on the opposing sidewalls 2025*a* and 2025*b* on the unit frame 2024. The guide rail 2200, which has a sectional U-shape, mounted to the walls on both sides of the guide rail 2023 and sliding member 2022 engagingly slides so the sliding member 2022 slidably moves along the guide rails 2023 from the setting position which protrudes outside of the unit frame 2024 of FIG. 23 to the reading position which is stored at a predetermined position inside of the unit frame 2024 of FIG. 25.

Figure 25:
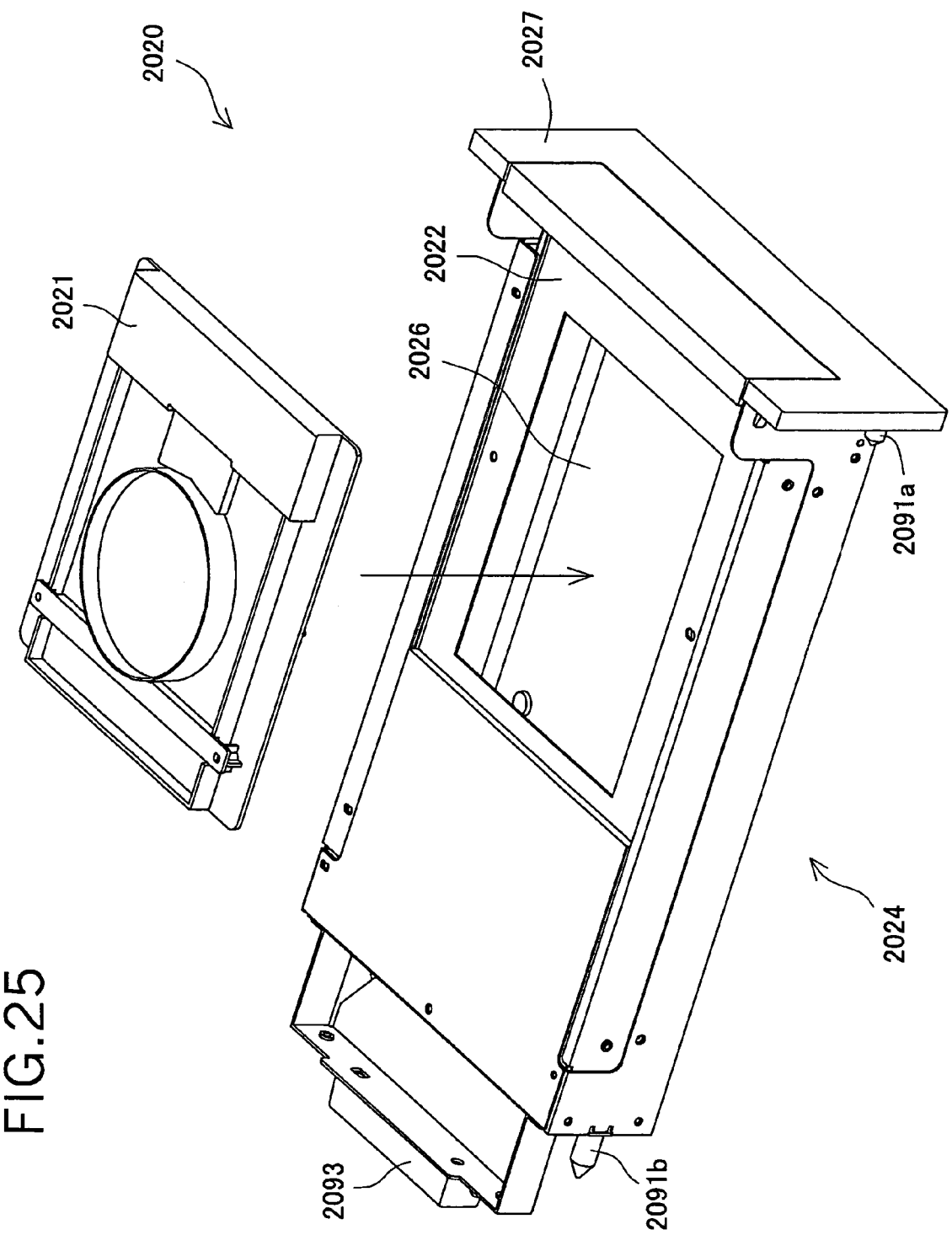
FIG. 25 is view showing a stage for a Petri dish mounted to the stage unit shown in FIG. 23.

The unit frame 2024 is unitized to the apparatus frame 2011. In this state, the sliding member 2022 is movably mounted to the apparatus frame 2011 to move between a predetermined position inside the apparatus from 2011 (reading position; see FIG. 18) and the setting position outside of the apparatus frame 2011. The sliding member 2022 is configured by a frame having an opening 2026 in the center. The stage 2021 is set in the opening 2026. A plurality of stages 2021 such as the stage for a sheet as described for the first embodiment is available as well as the stage 2021 for a Petri dish as shown in FIG. 25. The stage 2021 having a configuration corresponding to the sample is set in the opening 2026. Specifically, the reason for separating the sliding member 2022 and the stage 2021 is to enable reading a wide variety of samples by combining a stage 2021 that has the structure corresponding to the specimen into the sliding member 2022. Note that the stage 2021 shown in FIG. 25 is a stage for a Petri dish. Because this stage has the same configuration as the stage (10*a*) described for the first embodiments, a detailed description thereof is omitted.

Figure 21:
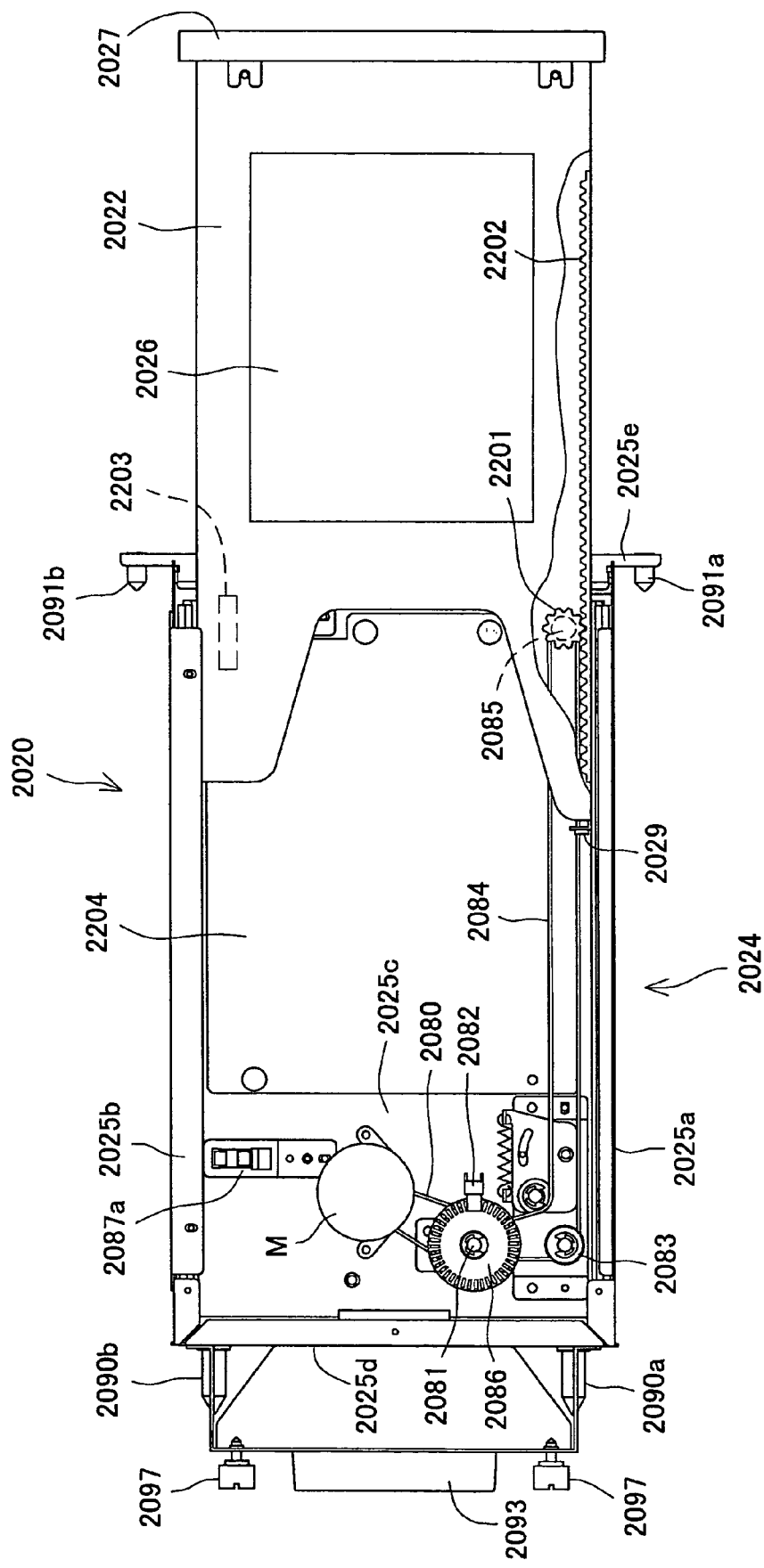
FIG. 21 is a plan view of a stage unit according to the second embodiment of the present invention.

The drive motor M that automatically moves the sliding member 2022 (stage 2021) to the setting position and to the reading position is mounted to the stage unit 2020. The bottom plate 2025*c* is established on the unit frame 2024 as shown in FIG. 21. The drive motor M is mounted to this bottom plate 2025*c*. Also, this drive motor M is fastened to the top of the bottom plate 25*c* on the opposite side of the setting position sandwiching the reading position. More specifically, when the stage unit 2020 is mounted to the apparatus frame 2011, the drive motor M is positioned in the backside of the apparatus frame 2011 (rear side) and on the front side of the apparatus from 2011, it is in a position enabling the sliding member 2022 to move between the reading position and the setting position.

Therefore, the drive motor M is mounted to the stage unit 2020 which is arranged in the middle area of the apparatus frame 2011 and is arranged to avoid the moving region of the sliding member 2020 (region between the setting position and the reading position). In other words, this is arranged at the backside of the apparatus frame 2011 where it will not hinder the movement of the sliding member 2022. Because it is not necessary to move in the area over the drive motor M, the sliding member 2022 moves between the setting position and the reading position at a lower position which makes the entire apparatus smaller in the height direction. Furthermore, this makes the distance between the setting position and the reading position shorter thereby enabling a shorter amount of processing time.

The following shall describe the relationships between the moving region of the scanning carriage 2060 and the moving region of the light source carriage 2040 and drive motor M.

Clearly depicted in FIG. 18, the region L1 represents the moving region of the scanning carriage 2060; L2 represents the moving region of the light source 2040. At least a portion of the moving region L1 of the scanning carriage 2016 and the moving region of the light source carriage 2040 overlap in the up and down directions of the drive motor M. In this way, the empty region outside of the moving region of the sliding member 2022 which is behind the stage 2021 in the middle area can be used as the setting region of the drive motor M thereby making this apparatus even more compact.

Note that as shown in FIG. 23, the guide rails 2200 of the sliding member 2022 extend the length D further behind the region supporting the stage 2021. In the same way as those described for the first embodiment, the guide rails 2200 and guide rails 2023 are engaged to support the sliding member 2022 which is positioned at the setting position. As shown in FIG. 18, the scanning carriage 2060, light source carriage 2040, and the sliding member 2022 move in the same direction, so the extended portion D, a moving region L1 of the scanning carriage 2060, and the moving region L2 of the light source carriage 2040 overlap in the up and down directions. This makes a more compact apparatus which is the same effect in the first embodiment.

A stepping motor that is capable of both forward and reverse rotations is configured for the drive motor M. The drive from this drive motor M is transmitted from its rotating shaft to the rotating shaft 2081 via the belt 2080. It is transmitted also from this shaft 2081 to the transmission belt 2084 that is trained between the pulleys 2083 and 2085. The pulleys 2083 and 2085 are arranged along the guide rail 2023 that is mounted to the sidewall 2025*a* on one side of the unit frame 2024. The gear 2201 which is mounted to the same shaft as the pulley 25 engages the rack 2202 that is formed on the inside of the sidewall of the sliding member 2022.

Therefore, the rotation of the drive motor M is transmitted to the transmission belt 24. This transmission belt 2084 rotatably travels along the guide rails 2023, so that the pulley 2085 that is trained to the transmission belt 2084, the gear 2201 on the same shaft, and the rack 2202 are engaged to reciprocally move the sliding member 2022 along the guide rail 2023. An encoder 26 is mounted on the rotating shaft 21. The photo-sensor is disposed to detect the slits of the encoder 26. Therefore, it is possible to ascertain the status of rotation of the rotating shaft 21 (number of rotations and angle) by detecting the slits of the encoder 26 using the photo-sensor 2082. The front cover 2027 is mounted to the sliding member 2022. Also, the stopper 2029 that abuts against the rear surface 2025d of the unit frame 2024 when the sliding member 2022 is positioned at the reading position is mounted to the rear side of the sliding member 2022. In other words, when the stopper 2029 abuts against the rear surface 2025d, the sliding member 2022 is securely positioned at the predetermined reading position.

Figure 22:
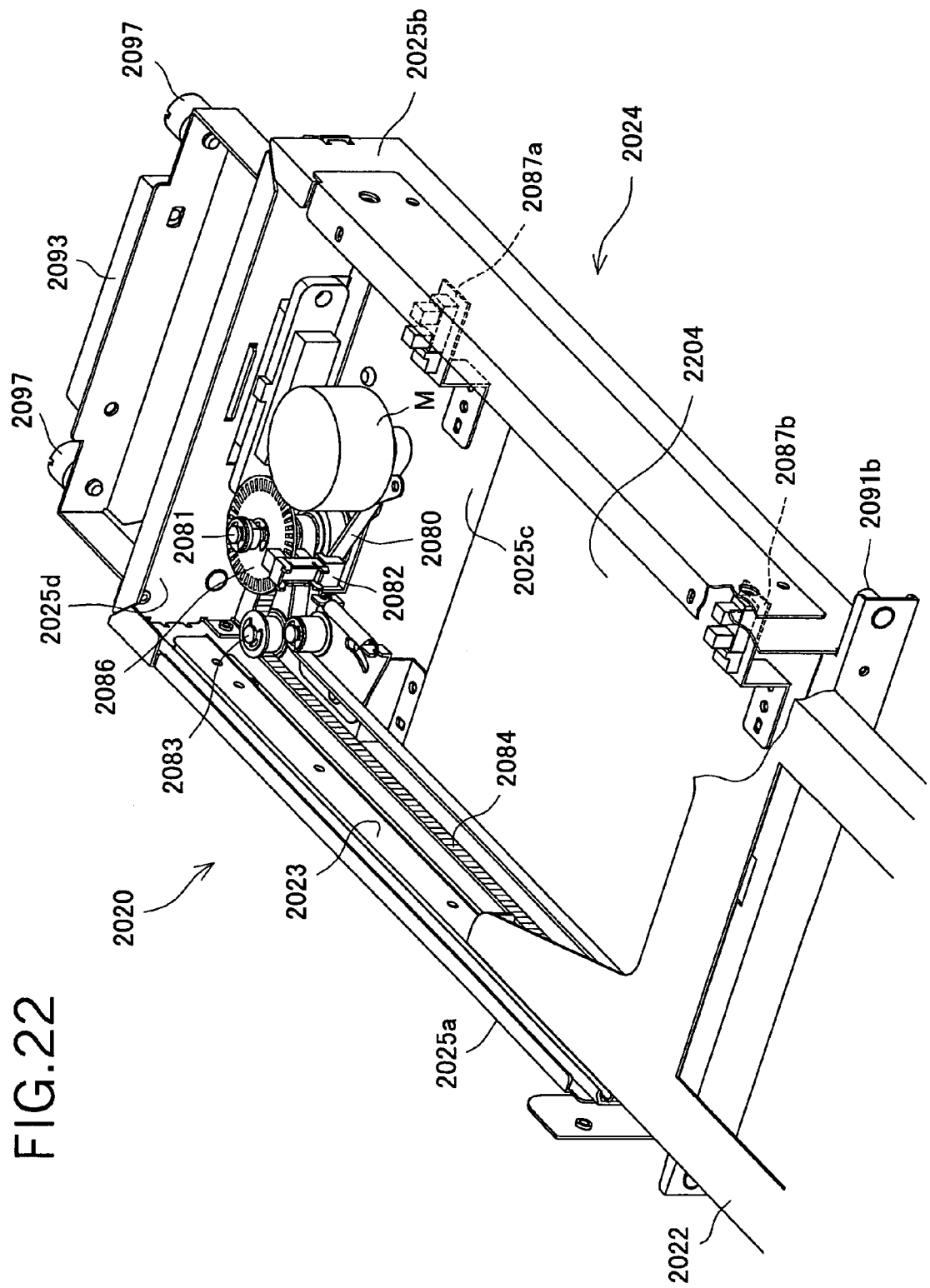
FIG. 22 is a perspective view of the stage unit according to the second embodiment of the present invention.

As shown in FIG. 21 and FIG. 22, a close sensor 2087a (position detection sensor) that operates when the sliding member 2022 is positioned near (on the setting position side only slightly away from the predetermined reading position) the reading position, an open sensor 2087b that operates when the sliding member 22 is at the setting position are both arranged with photo-sensors on the unit frame 2024. Also, as is indicated by hidden lines in the middle of FIG. 21, the rack 2203 is mounted to the upper backside surface of the sliding member 2022. Each of the closed sensor 2087a and the open sensor 2087b detects the rack 2203.

As described above, the stage unit 2020 is provided a unit frame 2024 that it is separate from the apparatus frame 2011. The sliding member 2022 that is equipped with the stage 2021 is supported and guided on the guide rail 2023 to slide on the unit frame.

To describe the mounting and positioning of the apparatus frame 2011 of the stage unit 2020 in more detail, the space is disposed in the apparatus frame 2011 to store the stage in the central area as described above. The stage 2020 is stored in this space, and is fastened to the apparatus frame 2011 (the casing 2010) using screws.

More specifically, as shown in FIG. 21, the pin-shaped protrusions 2090a, 2090b, 2091a, and 2191b on both sides of the opposing front sidewall 2025e and the area sidewall 2025d (two on each side) are equipped on the unit frame 2024. Also on the apparatus frame 2011 side are established the engaging holes 2094a, 2094b, 2095a, and 2095b that engage the protrusions 2090a, 2090b, 2091a and 2091b on the front wall and the rear wall. Therefore, the mounting positions of the frame apparatus 2011 and the unit frame 2024 of the stage unit 2020 are regulated by the mating of the protrusions 2090a, 2090b, 2091a and 2091b formed on the one side, and the engaging holes 2094a, 2094b, 2095a and 2095b that are-formed on the other side. Particularly, when reading images, it is necessary to arrange the sample within the depth of focus (sample reading position) to attain quality images. Using the positioning method described above, the position of the sample in the height direction is controlled, so that it is possible to position the sample within the depth of focus.

Figure 24:
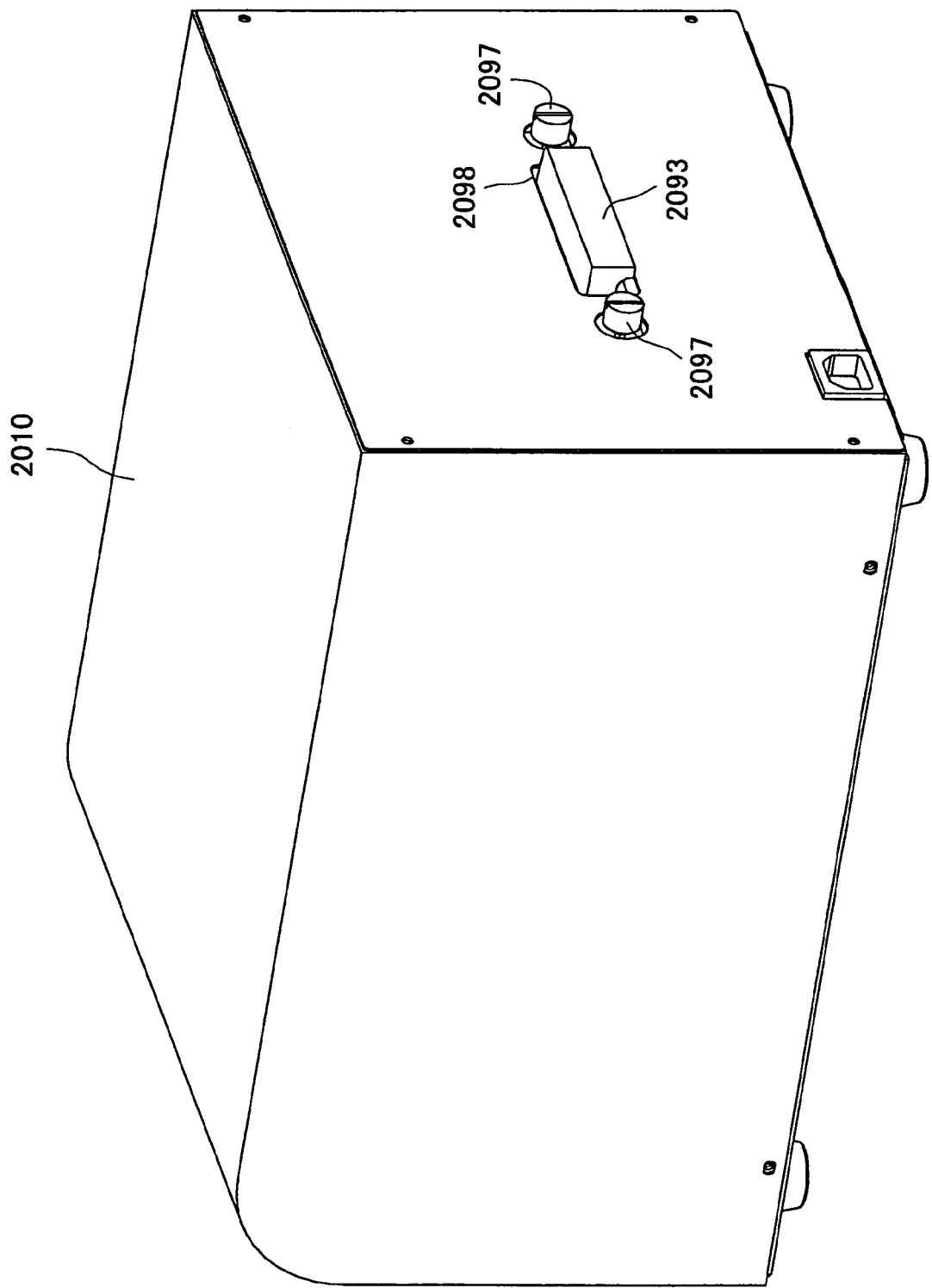
FIG. 24 is a perspective view from a backside of the image reading apparatus shown in FIG. 17.

Also, screw holes that mate with the screws 2097 are formed in the rear sidewall 2025d of the unit frame 2024. The casing 2010 and the unit frame 2024 are fastened together by screws 2097. Also, as shown in FIG. 21, the number 2093 represents a protruding pressing member which is established on the unit frame 2024. As shown in FIG. 24, the hole 2098 is formed on the casing 2010 through which this protruding pressing member 2093 passes. An operator removes the screws 2097 and manually presses the protruding pressing member 2093 toward the front side to remove the unit frame 24 from the apparatus frame 2011. This makes it easy to be removed from the apparatus frame 2011 while the casing 2010 is attached.

Figure 19:
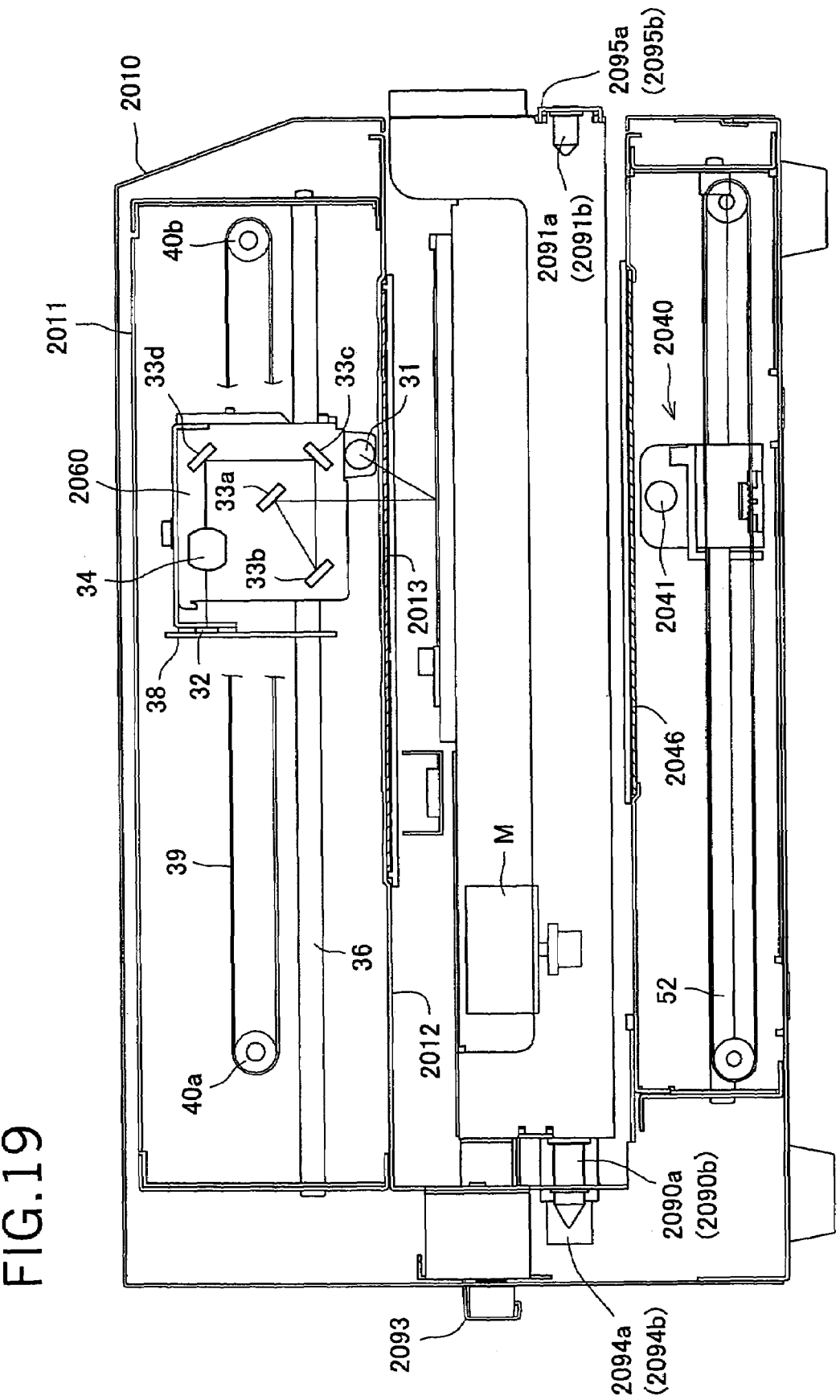
FIG. 19 is a view of an internal structural layout of the image reading apparatus shown in FIG. 17.

Next, to describe the light source carriage 2040, see FIG. 18 and FIG. 19. The light source carriage 2040 is incorporated into the lower area of the apparatus frame 2111. Two bar-shaped light sources 2041 are mounted thereupon to irradiate light from below onto the sample that is on the stage 2021. This light source carriage 2040 corresponds to the second carriage 51 describe in the first embodiment. In the same way as the second carriage 51, the light source carriage 2040 is guided by the guide member 52a(b), and reciprocally movable between the position indicated by solid line in FIG. 18 (home position) and the position indicated by hidden lines in the same drawing, in synchronization with the scanning carriage 2060. Note that the drive transmission system of the light source carriage 2040 is the same as the one described in the first embodiment, and thus a detailed description thereof is omitted.

A spacer wall made of transparent glass 2046 is established between the light source carriage to 2040 and the stage unit 2020. This prevents dust from entering the system. Note that according to this embodiment of the present invention, a diffusion plate 2204 is mounted to the bottom plate 2025c of the stage unit 2020. However, it is perfectly acceptable to use this transparent glass 2046 as the diffusion plate instead of the diffusion plate 2204. In such case, it is acceptable for the diffusion plate 2204 of the stage unit 2020 to be transparent glass.

The following shall describe the control of the drive motor M of the stage unit 2020, the scanning carriage 2060, and the light source carriage 2040. The drive motor M of the stage unit 2020 is configured by a stepping motor. It is possible to control the rotation of direction whether in the forward or reverse directions and the rotational speed by changing the pulse count of the drive power supply. Though not shown in the drawings, a stepping motor that is separate from the drive motor M is interlocked also to the scanning carriage 2060 and the light source carriage 2040. It is possible to control its forward or reverse directional rotation.

Figure 26:
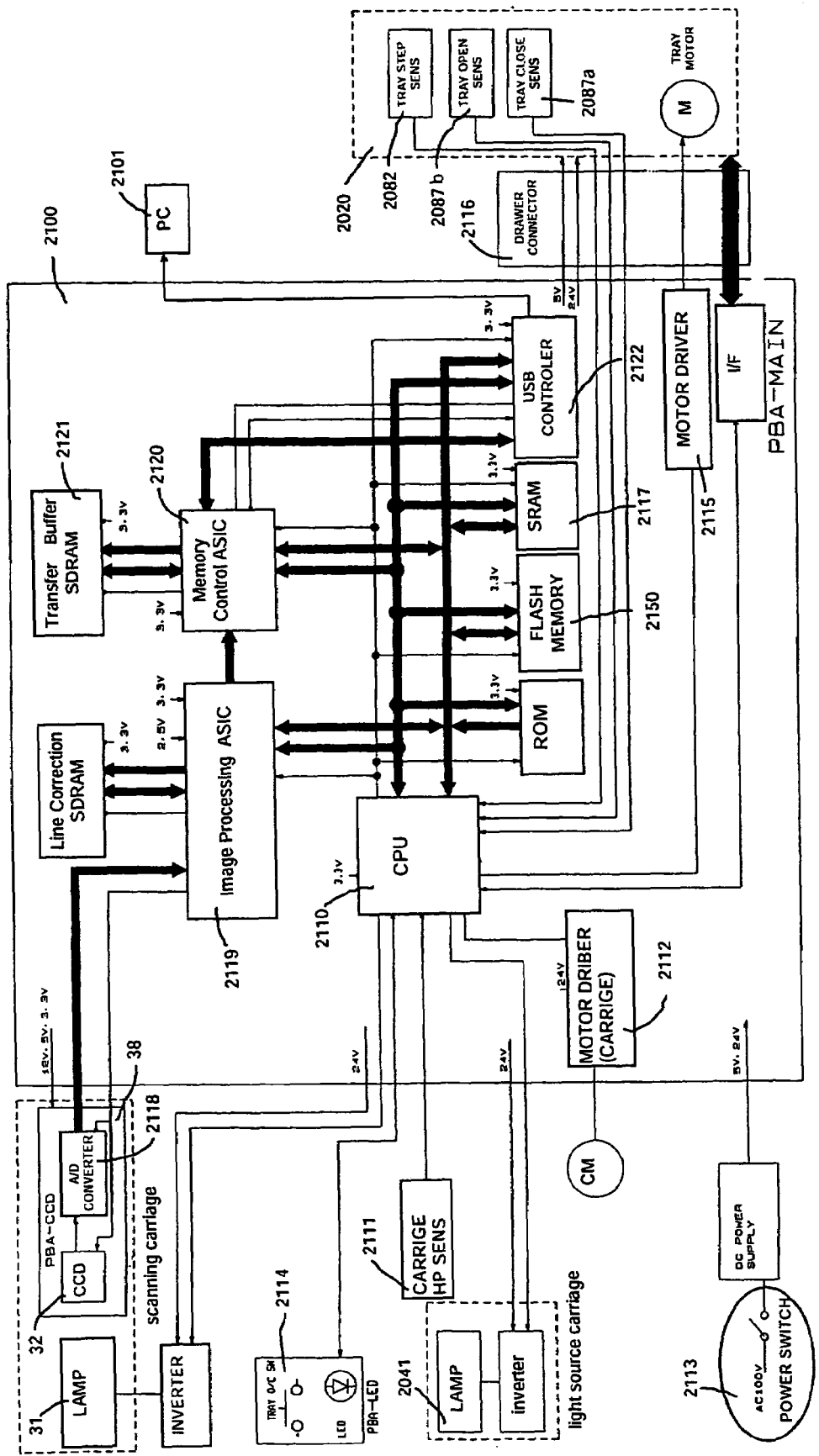
FIG. 26 is a block diagram of a control of the image reading apparatus according to the second embodiment of the present invention.

The description shall be in relation to FIG. 26. First, the controller 2100 controls the drive of each unit using the CPU 2110, and transfers image data output from the line sensor to an external apparatus such as a computer (see FIG. 26). Detection signals from the home position sensor 2111 of the scanning carriage 2060, detection signals from the open sensor 2087b and the close sensor 2087a of the stage unit 2020, and detection signals of the photo sensor 2082 which is arranged on the drive motor M encoder 2086 are connected for transmission. Also, the control CPU 2110 is connected to transmit command signals to the driver circuit 2112 of the scanning carriage 2060 and the light source carriage 2040, and to transmit command signals to the driver circuit 2115 of the drive motor M. Furthermore, a switch 2114 which is established on the front side of the apparatus is connected to the control CPU 2110. Signals from this switch 2114 are input.

Also, the control CPU 2110 controls the lighting and extinguishing of the first light source 31 via an inverter. The power supply is connected to the first light source 31 via the inverter. In the same way, the control CPU 2110 controls the lighting and extinguishing of the second light source 2041. Therefore, it is possible for the control CPU 2110 to turn on and off the first light source 31 or the second light source 2041, and to drive or stop the carriage drive motor M using commands from the control panel or an external apparatus 2101, such as a computer. Output values (analog data) of the line sensor 32 are converted at the A/D converter 2118 into digital data. At the image processor ASIC 2119, various correction processes are performed on that data which is then transferred to the transmission buffer SDRAM 2121. This data is transferred to the USB controller 2122 and then sent from the transmission buffer SDRAM 2121 to the external apparatus 2101 via memory control ASIC 2120.

The control CPU 2110 controls at least two levels of rotating speeds such as low-speed and high speed for the drive motor of the stage unit 2020 according to a control program that is stored in its flash memory 2150. The memory 2117 is disposed on the control CPU 2110. Shown in the drawing, this is configured of an SRAM (hereinafter referred to as memory) such as a writable EEPROM. A plurality of speed data that has been preset is stored in the memory 2117 (memory means). This control CPU 2110 selects one of the speed data selections that are stored in this memory to control the drive motor M according to that speed. According to this environment of the present invention, there are two speed levels stored in the memory 2117 for the stage 2021, namely low-speed, 130 mm/sec. (used when the sample is a liquid); and high-speed, 210 mm/sec. (used when the sample is a sheet). It should be noted here that the speed data in memory 2117 can be set to three or more levels according to the nature of the samples to be read. Speed data is not limited to only speed, rather it is perfectly acceptable to store a plurality of speed information (data corresponding to the speed of movement of the tray) such as pulse cycles that correspond to speed.

The control CPU 2110 selects one of the speeds that are stored in the memory 2117, then issues a cycle pulse signal that corresponds to that selected speed to the drive motor M driver circuit 2115. Note that the speed selection of the control CPU 2110 has the following configuration. An input switch (push switch) allows the operator to select the speed is established on the apparatus control panel. This selects the speed according to the signal from this switch or the apparatus can automatically detect the type of stage to select speed that corresponds to that detection results. Note that according to this embodiment of the present invention, the switch 2114 is established to open and close the tray 2021 (sliding member 2022). The control CPU 2110 detects the operating time of this switch 2114 (time it is pressed) and selects the speed data according to the amount of time operation. This is described in further detail below. This one switch can be used to select one from a plurality of speeds. This means that there are fewer numbers of switches which further enhances the ease of operation. Still further, it is also perfectly acceptable to equip the apparatus with a dial that can allow the user to continuously select speeds by rotating it.

Also, there are already preset default data for speeds in the memory 2117. However, the configuration allows speed data to be set according to the conditions of use via an operation panel or an external apparatus input means such as a computer to rewrite the speed data. Shown in the drawing, the control CPU 2110 calls up the speed data that is stored as preset initial values from the memory 2117 and sends it to a computer which is an external apparatus. On the computer side, the new speed data is input using an input board to store that new speed data in the memory 2117. Note that it is also perfectly acceptable for the control CPU 2110 to rewrite the speed data of the memory 2117 by communicating with the external apparatus to provide it non-quantitative, sensory information such as "increasing speed," or "decreasing speed."

Next, the control CPU 2110 controls the drive motor to stop so that it will stop stage unit 2020 highly accurately at the reading position. A close sensor 2087a is equipped on the stage unit 2020. This detects whether the stage 2021 is positioned near the reading position (the closed position). Therefore, it is possible for the control CPU 2110 to stop the drive motor M based on the detection signal from this close sensor 2087a to stop the stage 2021 at the reading position. In that case, the mounting of the sensor for the stopping position of the staged 2021 can greatly affect positioning accuracy. For that reason, if the stage is not accurately stopped at the predetermined stopping position, the reading starting position will be incorrect which can cause problems such as affecting the precision of the data that is read.

Shown in the drawing, the stopper 2029 is established on the sliding member 2022, as described above. Therefore, the stopper 2029 strikes the inner wall of the apparatus frame 2011 intentionally, thereby causing a power swing in the drive motor M. The drive motor M is then stopped after a power swing is detected, thereby accurately stopping the sliding member 2022 (stage 2021) at the predetermined reading position. The following shall provide a more detailed description of this configuration.

Figure 27:
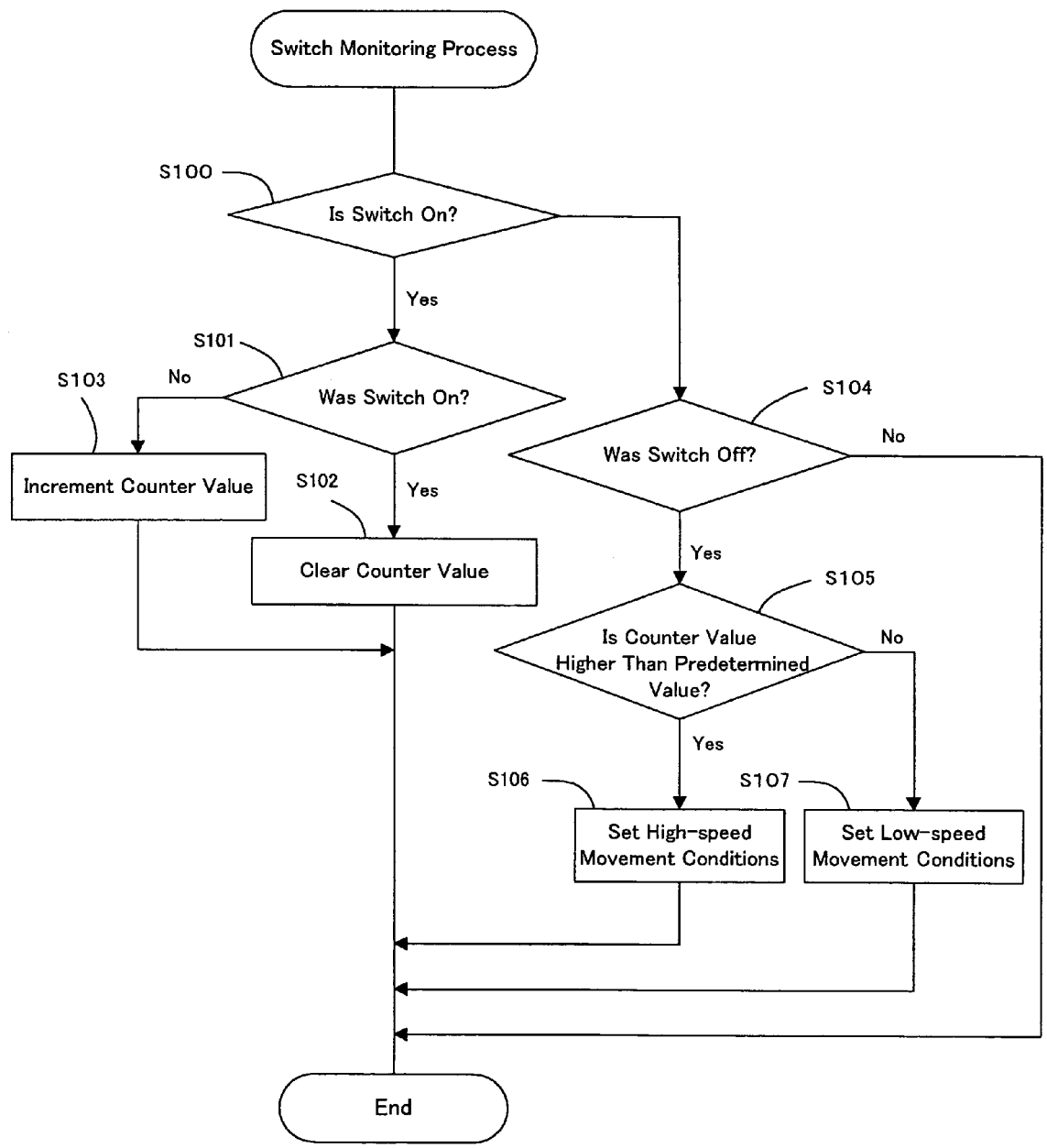
FIG. 27 is a flowchart for explaining a process of setting a movement speed of the stage according to the second embodiment of the present invention.
Figure 28:
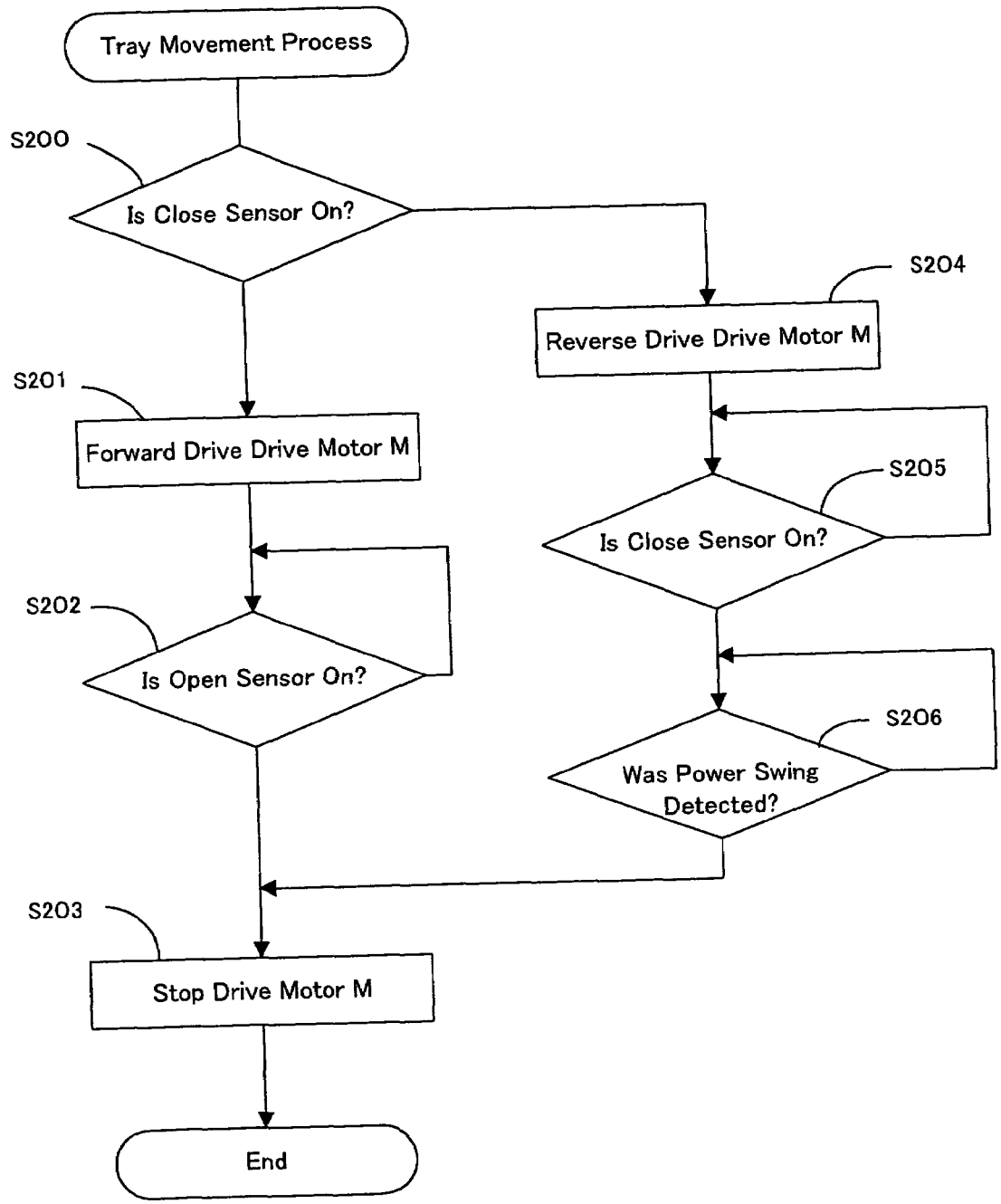
FIG. 28 is a flowchart for explaining a process of controlling a movement of the stage according to the second embodiment of the present invention.

The following shall now explain in detail the setting for movement speed of the stage 2021, and its control of movement based on FIG. 27 and FIG. 28. FIG. 27 is a flowchart showing the selection of movement speeds of the stage 2021. Again, according to this embodiment of the present invention, the speed of movement of the stage 2021 selected from the two speeds of high speed and low speed based on the results of detection of the operating time of the switch 2114 (push switch) established on the front of the apparatus. To describe in detail, when the stage 2021 which is at the reading position is moved to the setting position, or when the stage 2021 is at the setting position and is moved to the reading position, the switch 2114 is pressed. If the amount of time of its operation (the time it is pressed) is longer than a predetermined amount of time, the speed of movement of the stage 2021 is determined to be high speed. Conversely, if the amount of time of its operation is shorter than a predetermined amount of time, the speed of movement of the stage 2021 is determined to be a low-speed. Note that according to this embodiment of the present invention, the control CPU 2110 is set to monitor the status of the switch 2114 at a predetermined timing (for example, every five seconds). By repeating the switch monitoring process flow outlined in FIG. 27, the CPU detects the amount of time of operation of the switch 2114.

First, the control CPU 2110 judges whether the switch 2114 is on (that the switch is pressed) at step S100. If it is judged to be on, it is judged that it was off at the previous monitoring. If it was judged to be off in the previous time at step S101, it clears the count value of the counter incorporated in the control CPU 2110 (S102). Specifically, if it is judged at step S101 to be off, then it is judged that the switch 2114 has shifted from an off state to on state. More specifically, it is judged that the operation (pressing of the switch) of the switch 2114 has started and it resets the counter to zero to measure the amount of time of switch operation from then.

If it is judged to be on in the previous time at step S101, it increments the count value of the counter (S103). Specifically, it judges that the on state from the previous monitoring has been maintained by the switch 2114 and increases the counter value because it continues to measure the amount of time of switch operation. In this way, the steps of S100, S101, and S103 are repeated while the switch 2114 is operated to measure the amount of time that it is operated.

If the switch 2114 is judged to be off at step S100, it is determined that the switch is on at the previous monitoring (S104). If determined that the switched 2114 is off, in other words, the off state has continued from the previous monitoring, and monitoring remains stopped. In other words, it is judged that the switch 2114 has not been operated by the user.

Also, if the judgment at step S104 is on from the previous monitoring, the counter is compared value with the set value (predetermined value) that is preset to judge whether the counter value is higher than the set value (S105). To describe this in other words, the switch 2114 has shifted from an on state to off state. This determines that the pressing of this switch 2114 has ended and it whether the operation time is higher than the set value (predetermined time). According to this embodiment of the present invention, the set value is set to 160 (=800 msec./5 msec.) that corresponds to 800 msec. The control CPU 2110 selects high-speed when the count value is higher than the set value and sets the conditions for high-speed movement (S106). Conversely, if the account value is less than the predetermined value, the control CPU 2110 selects the low-speed and sets the conditions for low-speed movement (S107). In other words, when the control CPU 2110 judges that the switch 2114 has been pressed for longer than 800 msec., the CPU selects the faster stage speed from the memory 2117 (according to this embodiment that speed is 210 mm/sec.), then sets the conditions such as the pulse cycles that correspond to that speed (in this embodiment, 500 pps). If it is judged to be less than 800 msec., the CPU selects the slower stage speed from the memory 2117 (according to this embodiment that speed is 130 mm/sec.) and sets the conditions such as the pulse cycles that correspond to that speed (in this embodiment, 300 pps).

With this embodiment, the optimum values are found from the actual testing values that correspond to the nature of the sample. The initial values are set to 130 mm/sec. and to 210 mm/sec. However, it is possible to set this to faster or slower speeds according to the ambient environment of use and the status of the sample to be read. In this case, for example, the control CPU 2110 writes the data of the memory 2117 based on the data input from an external apparatus that is connected to the image reading apparatus. After setting (selecting) the speed of movement of the stage 2021, the control CPU 2110 drives the drive motor M by inputting the cycle pulse signal that corresponds to the speed of movement of the stage selected in the drive motor M driver circuit 2115.

The following shall describe the flow of movement control of the stage 2021 shown in FIG. 28. After first setting the speed of movement, the control CPU 2110 executes the following operations. First, it judges whether the close sensor 2087a is on (S200). If the close sensor 2087a is on (specifically, when the stage 2021 is positioned at the reading position), the control CPU 2110 inputs the drive pulse signals that correspond to the speed of movement that is set (selected) first, to the drive motor M to rotate it in the forward direction, thereby moving the stage 2021 to the setting position (S201).

Next, the control CPU 2110 continues rotating the drive motor M until it receives the on signal from the open sensor 2087b to move the stage 2021 toward the setting position at the set speed (S202). Next, the control CPU 2110 stops the issuing of drive pulse signals to the drive motor M when it receives the on signal from the open sensor 2087b to stop the drive of the drive motor M (S203). In other words, the stage 2021 is stopped at the setting position.

On the other hand, at step S200, when the close sensor 2087a is off (specifically, when the stage 2021 is positioned at the setting position), the control CPU 2110 inputs the drive pulse signals to the drive motor M that correspond to the speed of movement that is set (selected) first to the drive motor M to rotate in the reverse direction to move the stage 2021 to the reading position (S204). The control CPU 2110 continues (S205) rotating the drive motor M until it receives the on signal from the close sensor 2087a. When the on signal has been received from the close sensor 2087a, it judges whether an overload has been applied to the drive motor M, or in other words that the stopper 2029 has abut against the rear surface 2025d of the unit frame 2024, thereby causing the drive motor M to experience a power swing (S206). If the power swing has been detected, the control CPU 2110 stops the issuing of the drive pulse signals to the drive motor M to stop the drive motor (S203).

The following procedures are applied to judge power swing detection at step S206.

First, the control CPU 2110 starts counting the pulse signals (hereinafter referred to as drive pulse signals) that are (1) input to the drive motor M at the on signal from the close sensor 2087a. At the same time, the control CPU 2110 starts counting the pulse signals (hereinafter referred to as rotation pulse signals) from the photo-sensor 2082 using the detection of the slit on the encoder 2086 established on the drive shaft 81. Again, according to the embodiment described above, there are ten slits formed in the encoder 2086. Two pulses of the rotational pulse signal are counted for the nine counts (9 pulses) of the drive pulse signals.

Also, (2) when the drive pulse signals have reached 18 pulses, it is judged whether the count number of the rotational pulse signals is within a predetermined range (according to this embodiment, it is strictly 2 times because of the design, however it can be 1 to 5 times considering the error for sensor mounting and accuracy of the sensors). (3) If judged to be within the predetermined range, the drive motor M is rotated in the forward direction (namely the stopper 2029 has not abut against the rear surface 2025d of the unit frame 2024, and the drive motor M has not entered a power swing), the CPU continues driving the drive motor M. (4) If it is judged to be outside of the predetermined range, it is judged that the drive motor M is experiencing a power swing. In this way, power swings of the motor (overloads states) are detected some by performing the steps (1) to (4) for each count of the drive pulse signals 18 from the control CPU 2110 until the power swing of the drive motor M has been detected. Thus, the stage 2021 is accurately stopped at the predetermined reading position.

Also, it is possible to control this in the following way by periodically performing the power swing routine of (1) to (4) at predetermined time intervals.

At step S200, it is judged that the close sensor 2087a is off and the stage 2021 is moved to the reading position (S204). When a power swing is detected in the drive motor M (overload of the drive motor M) during that movement, and the close sensor 2087a does not detect the stage 2021, the control CPU 2110 rotates the drive motor M in reverse to move the stage 2021 to the setting position. Specifically, while the stage 2021 is moving from the setting position to the reading position, the steps described above, namely (1) to (4), are periodically executed to monitor whether an erroneous load is being applied to the drive motor M. In the event that a power swing has been judged at step (4), after stopping the drive motor M, it is rotated in reverse to move the stage 2021 toward the setting position.

In that case, the power swing has been detected and the close sensor 2087a has not detected the stage 2021. This means that the stage 2021 is between the setting position and the reading position, and that the sample has become caught in the operator's hand and that the drive motor M (the stage 2021 has stopped) is not rotating regardless of the input of drive pulses to the drive motor M. Therefore, using this control, this reduces the scattering of the sample inside the apparatus, if the sample should fall on the stage 2021, and it prevents injury to the operator.

The disclosures of Japanese Patent Applications No. 2003-326697 filed on Sep. 18, 2003, No. 2003-428193 filed on Dec. 24, 2003, No. 2003-428194 filed on Dec. 24, 2003, No. 2003-428195 filed on Dec. 24, 2003, No. 2003-428196 filed on Dec. 24, 2003, No. 2004-226355 filed on Aug. 3, 2004, and No. 2004-226356 filed on Aug. 3, 2004 are incorporated herein.

While the invention has been explained with reference to the specific embodiments of the invention, the explanation is illustrative and the invention is limited only by the appended claims.

What is claimed is:

1. An image reading apparatus comprising:
   an apparatus frame,
   a stage for placing a specimen movably supported on the apparatus frame, said stage moving between a setting position for placing and removing the specimen and a reading position for reading the specimen,
   a light source disposed adjacent to the stage for irradiating light onto the specimen on the stage,
   photoelectric conversion means having an elongated shape for photo-electrically converting the light reflected from the specimen,
   optical means disposed adjacent to the photoelectric conversion means for guiding the light from the specimen to the photoelectric conversion means,
   a carriage for mounting the optical means movably supported on the apparatus frame, said carriage moving along the stage substantially same as a moving direction of the stage, and
   a drive motor for moving the stage, said carriage moving above the stage, said drive motor being arranged below a moving region of the carriage so that at least a portion of the drive motor overlaps the moving region of the carriage in a vertical direction.

2. An image reading apparatus according to claim 1, further comprising a first guide member for slidably supporting the carriage, and a second guide member for slidably supporting the stage, said first and second guide members being supported on the apparatus frame parallel in a same direction.

3. An image reading apparatus comprising:
   an apparatus frame,
   a stage for placing a specimen movably supported on the apparatus frame, said stage moving between a setting position for placing and removing the specimen and a reading position for reading the specimen,
   a light source disposed adjacent to the stage for irradiating light onto the specimen on the stage,
   photoelectric conversion means having an elongated shape for photo-electrically converting the light reflected from the specimen,
   optical means disposed adjacent to the photoelectric conversion means for guiding the light from the specimen to the photoelectric conversion means,
   a carriage for mounting the optical means movably supported on the apparatus frame, said carriage moving along the stage substantially same as a moving direction of the stage,
   a drive motor for moving the stage,
   control means for controlling the drive motor, and
   speed selection means for selecting a movement speed of the stage among at least two different speeds, said control means controlling the drive motor according to the movement speed selected by the speed selection means.

4. An image reading apparatus according to claim 3, wherein said speed selection means includes a push switch and detection means for detecting an operating time of the push switch, said control means controlling the drive motor according to a detection result of the detection means.

* * * * *